(12) United States Patent
Reiter et al.

(10) Patent No.: US 6,992,176 B2
(45) Date of Patent: Jan. 31, 2006

(54) ANTIBODY HAVING A T-CELL RECEPTOR-LIKE SPECIFICITY, YET HIGHER AFFINITY, AND THE USE OF SAME IN THE DETECTION AND TREATMENT OF CANCER, VIRAL INFECTION AND AUTOIMMUNE DISEASE

(75) Inventors: Yoram Reiter, Haifa (IL); Galit Denkberg, Nofit (IL)

(73) Assignee: Technion Research & Development Foundation Ltd., Haifa (IL)

( * ) Notice: Subject to any disclaimer, the term of this patent is extended or adjusted under 35 U.S.C. 154(b) by 478 days.

(21) Appl. No.: 10/073,301

(22) Filed: Feb. 13, 2002

(65) Prior Publication Data

US 2005/0255101 A1   Nov. 17, 2005

(51) Int. Cl.
*C07K 16/28* (2006.01)
*C07K 16/30* (2006.01)

(52) U.S. Cl. .............................. 530/388.22; 530/388.7
(58) Field of Classification Search ............. 530/391.1, 530/389.4, 389.7, 391.3, 391.7, 388.22, 388.7; 424/143.1, 178.1, 155.1, 159.1, 179.1, 181.1
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |

FOREIGN PATENT DOCUMENTS

EP    1178116 A1 *  2/2002

WO    WO 95/29193 A2 * 11/1995
WO    WO 97/02342       1/1997

OTHER PUBLICATIONS

Harlow and Lane. Antibodies, A Laboratory Manual. 1998, Cold Spring Harbor Laboratory, USA, p. 287.*

Remington's Pharmaceutical Sciences 18th Edition. 1990, Gennaro, A. R., Ed., Mack Printing Co., Easton, PA, p. 1579.*

Rammensee et al. MHC Ligands and Peptide Motifs. 1997, Springer, NY, pp. 235-281.*

Andersen et al, "A recombinant antibody with the antigen-specific, major histocompatibility complex-restricted specificity of T cells", Proc Natl Acad Sci U S A. Mar. 5, 1996;93(5):1820-4.

Chames et al, "Direct selection of a human antibody fragment directed against the tumor T-cell epitope HLA-A1-MAGE-A1 from a nonimmunized phage-Fab library", Proc Natl Acad Sci U S A. Jul. 5, 2000;97(14)7969-74.

Reiter et al, "Peptide-specific killing of antigen-presenting cells by a recombinant antibody-toxin fusion protein targeted to major histocompatibility complex/peptide class I complexes with T cel receptor-like specificity", Proc Natl Acad Sci U S A. Apr. 29, 1997;94(9)4631-6.

Cohen, et al, "Direct detection and quantitation of a distinct T-cell epitope derived from tumor-specific epithelial cell-associated mucin using human recombinant antibodies endowed with the antigen-specific, major histocompatibility complex-restricted specificity of T cells", Cancer Res. Oct. 15, 2002;62(20):5835-44.

* cited by examiner

*Primary Examiner*—Christina Chan
*Assistant Examiner*—Marianne DiBrino

(57) ABSTRACT

An isolated molecule which comprises an antibody specifically bindable with a binding affinity below 20 nanomolar, preferably below 10 nanomolar, to a human major histocompatibility complex (MHC) class I being complexed with a HLA-restricted antigen and optionally further comprises an identifiable or therapeutic moiety conjugated to the antibody.

1 Claim, 8 Drawing Sheets

Figure 1A:
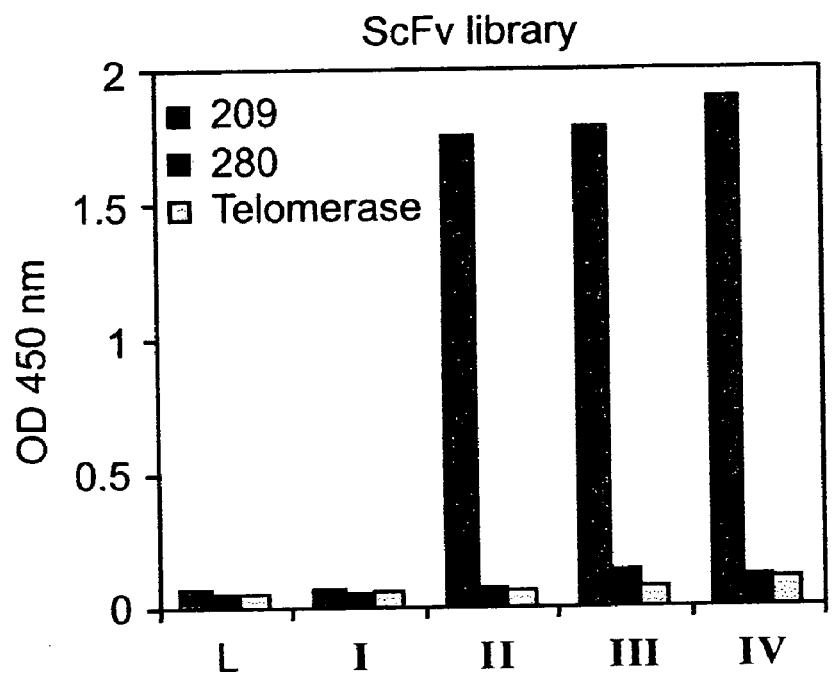

```
  1   2   3   4   5   6   7   8   9  10  11  12  13  14
CAG GTG AAA CTG CAG GAG TCT GGG GGA GGC TTA GTG AAG CCT   SEQ ID NO:8
gln val lys leu gln glu ser gly gly gly leu val lys pro   SEQ ID NO:9

15  16  17  18  19  20  21  22  23  24  25  26  27  28
GGA GGG TCC CTG AAA CTC TCC TGT GCA GCC TCT GGA TTC ACT
gly gly ser leu lys leu ser cys ala ala ser gly phe thr 29  30  31  32  33  34  35  36  37  38  39  40  41  42
TTC AGT AGC TAT GGC ATG TCT TGG GTT CGC CAG ACT CCA GAC
phe ser ser tyr gly met ser trp val arg gln thr pro asp 43  44  45  46  47  48  49  50  51  52  53  54  55  56
AAG AGG CTG GAG TGG GTC GCA ACC ATT AGT AGT GGT GGT AGT
lys arg leu glu trp val ala thr ile ser ser gly gly ser 57  58  59  60  61  62  63  64  65  66  67  68  69  70
TAC ACC TAC TAT CCA GAC AGT GTG AAG GGG CGA TTC ACC ATC
tyr thr tyr tyr pro asp ser val lys gly arg phe thr ile 71  72  73  74  75  76  77  78  79  80  81  82  83  84
TCC AGA GAC AAT GCC AAG AAC ACC CTG TAC CTG CAA ATG AGC
ser arg asp asn ala lys asn thr leu tyr leu gln met ser 85  86  87  88  89  90  91  92  93  94  95  96  97  98
AGT CTG AAG TCT GAG GAC ACA GCC ATG TAT TAC TGT GCA AGA
ser leu lys ser glu asp thr ala met tyr tyr cys ala arg 99 100 101 102 103 104 105 106 107 108 109 110 111 112
GGT AAC TGG GAA GGA TGG TAC TTC GAT GTC TGG GGC CAA GGG
gly asn trp glu gly trp tyr phe asp val trp gly gln gly 113 114 115 116 117 118
ACC ACG GTC ACC GTC TCC TCA GGT GGA GGC GGT TCA GGC GGA
thr thr val thr val ser *ser gly gly gly gly ser gly gly*

1   2   3   4   5   6
GGT GGC TCT GGC GGT GGC GGA TCG AAC ATC GAG CTC ACT CAG
*gly gly ser gly gly gly gly ser* asn ile glu leu thr gln 7   8   9  10  11  12  13  14  15  16  17  18  19  20
TCT CCA GCA ATC ATG TCT GCA TCT CCA GGG GAG AGG GTC ACC
ser pro ala ile met ser ala ser pro gly glu arg val thr 21  22  23  24  25  26  27  28  29  30  31  32  33  34
ATG ACC TGC AGT GCC AGC TCA AGT ATA CGT TAC ATA TAT TGG
met thr cys ser ala ser ser ser ile arg tyr ile tyr trp 35  36  37  38  39  40  41  42  43  44  45  46  47  48
TAC CAA CAG AAG CCT GGA TCC TCC CCC AGA CTC CTG ATT TAT
tyr gln gln lys pro gly ser ser pro arg leu leu ile tyr 49  50  51  52  53  54  55  56  57  58  59  60  61  62
GAC ACA TCC AAC GTG GCT CCT GGA GTC CCT TTT CGC TTC AGT
asp thr ser asn val ala pro gly val pro phe arg phe ser
```

Fig. 3a

```
63  64  65  66  67  68  69  70  71  72  73  74  75  76
GGC AGT GGG TCT GGG ACC TCT TAT TCT CTC ACA ATC AAC CGA
gly ser gly ser gly thr ser tyr ser leu thr ile asn arg 77  78  79  80  81  82  83  84  85  86  87  88  89  90
ATG GAG GCT GAG GAT GCT GCC ACT TAT TAC TGC CAG GAG TGG
met glu ala glu asp ala ala thr tyr tyr cys gln glu trp 91  92  93  94  95  96  97  98  99  100 101 102 103
AGT GGT TAT CCG TAC ACG TTC GGA GGG GGG ACA AAG TTG
ser gly tyr pro tyr thr phe gly gly gly thr lys leu
```

ANTIBODY HAVING A T-CELL RECEPTOR-LIKE SPECIFICITY, YET HIGHER AFFINITY, AND THE USE OF SAME IN THE DETECTION AND TREATMENT OF CANCER, VIRAL INFECTION AND AUTOIMMUNE DISEASE

FIELD AND BACKGROUND OF THE INVENTION

The present invention relates to an antibody having a T-cell receptor specificity and higher affinity, conjugates of same with identifiable and/or therapeutic moieties, method of making the antibody and the conjugates, polynucleotides encoding the antibody and conjugates and methods of using the conjugates in the detection and treatment of cancer, viral infection and autoimmune disease.

The expression of specific peptides in complex with major histocompatibility complex (MHC) class I molecules on cells was shown to be associated with cancer and autoimmune disorders (1–3) and viral infections. In cancer, the discovery of these peptides emerged from the now well-established observation that human tumor cells often express antigens that are recognized by cytotoxic T lymphocytes (CTLs) derived from patients (1–5).

Moreover, it has been demonstrated that the immune response against the tumor is insufficient to cause tumor regression and that tumor cells can develop effective mechanisms to escape such an immune attack (6–9). Therefore, numerous approaches are being developed in the field of tumor vaccination in an attempt to augment the antitumor immune responses, including cancer peptide vaccines, autologous cancer vaccines, and the cancer-dendritic cell hybrid vaccine (7, 10, 11).

Because the specificity of the immune response is regulated and dictated by these class I MHC-peptide complexes, it should be possible to use these very specific and unique molecular cell-surface markers as targets to eliminate the cancer cells, while sparing the normal cells. A similar approach can be undertaken to eradicate viral infected cells and cells presenting targets for autoimmune attack. Thus, it would be very desirable to devise new molecules in a soluble form that will mimic the fine, unique specificity of the T-cell antigen receptor (TCR) to the cancer/viral/autoimmune-associated MHC-peptide complexes.

One promising approach is to generate recombinant antibodies that will bind the MHC-peptide complex expressed on the cancer cells surface with the same specificity as the TCR. These unique antibodies can subsequently be armed with an effector cytotoxic moiety such as a radioisotope, a cytotoxic drug, or a toxin. For example, antibodies that target cancer cells were genetically fused to powerful toxins originating from both plants and bacteria, thus generating molecules termed recombinant immunotoxins (12).

Antibodies with the MHC-restricted specificity of T cells are rare and have been difficult to generate by conventional hybridoma techniques because B cells are not educated to be self-MHC-restricted (13–16). The advantages of antibody phage-displayed technology makes it possible to also select large antibody repertoires for unique and rare antibodies against very defined epitopes. This has be demonstrated by the ability to isolate by phage display a TCR-like restricted antibody to a murine class I MHC H-2K$^k$ complexed with a viral epitope (17). Evidently, this antibody, being directed at mouse MHC, is useless in the treatment and diagnosis of humans. So far, attempts made by the same group to develop a TCR-like restricted antibody to a human class I MHC have failed. More recently an antibody was isolated reactive with the melanoma antigen MAGE-A1 in a complex with HLA-A1; however this antibody exhibited a low affinity and could be used to detect the specific complexes on the surface of antigen-presenting cells only when expressed in a multimeric form on a phage and not as a soluble antibody (18).

There is thus a widely recognized need for, and it would be highly advantageous to have, a TCR-like restricted antibody to a human class I MHC devoid of the above limitations.

SUMMARY OF THE INVENTION

In recent years, many cancer-associated, viral and autoimmune associated MHC-restricted peptides have been isolated and because of their highly restricted fine specificity, they are desirable targets for novel approaches in immunotherapy and immunodiagnosis. Antibodies that are able to recognize cancer-associated, viral and autoimmune associated MHC-peptide complexes, with the same specificity as the T-cell antigen receptor, would be valuable reagents for studying antigen presentation by tumor cells, viral infected cells and autoimmune related cells, for visualizing MHC-peptide complexes on such cells, and eventually for developing new targeting agents for cancer, viral and autoimmune immunotherapy and immunodiagnosis.

While reducing the present invention to practice, and in order to generate exemplary molecules with such a unique, fine specificity, HLA-A2 transgenic mice were immunized with a soluble single-chain HLA-A2, complexed with a common antigenic T cell HLA-A2-restricted epitope derived from the melanoma differentiation antigen gp100. Using phage display, a high affinity recombinant scFv antibody that exhibits a characteristic TCR-like binding specificity to the gp100-derived epitope, yet unlike TCRs, it does so with an affinity in the nanomolar range was isolated. The TCR-like antibody recognizes the native MHC-peptide complex expressed on the surface of antigen-presenting cells. Moreover, when fused to a very potent cytotoxic effector molecule in the form of a truncated bacterial toxin, it was able to specifically kill antigen-presenting cells in a peptide-dependent manner and with TCR-like specificity. These results demonstrate, for the first time, the ability to isolate high-affinity human recombinant antibodies with the antigen-specific, MHC-restricted specificity of T cells directed toward human cancer T-cell epitopes. The selected TCR-like antibodies are useful for monitoring and visualizing the expression of specific MHC-peptide complexes on the surface of tumor cells, other cells presenting antigens, and lymphoid tissues, as well as for developing a new family of targeting agents for immunotherapy.

Hence, according to one aspect of the present invention there is provided an isolated molecule comprising an antibody specifically bindable with a binding affinity below 20 nanomolar, preferably below 10 nanomolar, to a human major histocompatibility complex (MHC) class I being complexed with a HLA-restricted antigen.

According to further features in preferred embodiments of the invention described below, the isolated molecule further comprising an identifiable moiety being conjugated to the antibody.

According to still further features in the described preferred embodiments the isolated molecule further comprising a therapeutic moiety being conjugated to the antibody.

In one example, the antibody is a single chain antibody having an amino acid sequence as set forth in SEQ ID NO:9.

According to another aspect of the present invention there is provided a pharmaceutical composition comprising a therapeutically effective amount of a molecule which comprises an antibody specifically bindable with a binding affinity below 20 nanomolar to a human major histocompatibility complex (MHC) class I being complexed with a HLA-restricted antigen, the molecule further comprises a therapeutic moiety being conjugated to the antibody. Preferably, the pharmaceutical composition further comprising a pharmaceutically acceptable carrier.

According to yet another aspect of the present invention there is provided a diagnostic composition comprising a molecule which comprises an antibody specifically bindable with a binding affinity below 20 nanomolar to a human major histocompatibility complex (MHC) class I being complexed with a HLA-restricted antigen, the molecule further comprises an identifiable moiety being conjugated to the antibody.

According to still another aspect of the present invention there is provided an isolated molecule comprising a first polynucleotide encoding an antibody specifically bindable with a binding affinity below 20 nanomolar to a human major histocompatibility complex (MHC) class I being complexed with a HLA-restricted antigen.

In one example, the first polynucleotide encodes a protein having an amino acid sequence as set forth in SEQ ID NO:9. In a specific example, the first polynucleotide has a nucleic acid sequence as set forth in SEQ ID NO:8.

According to further features in preferred embodiments of the invention described below, the isolated molecule further comprising a second polynucleotide being linked to the first polynucleotide and encoding a therapeutic moiety.

According to alternative features in preferred embodiments of the invention described below, the isolated molecule of claim 24, further comprising a second polynucleotide being linked to the first polynucleotide and encoding an identifiable moiety.

According to still further features in the described preferred embodiments the identifiable moiety is selected from the group consisting of a member of a binding pair and a label.

According to still further features in the described preferred embodiments the member of the binding pair is an antigen.

According to still further features in the described preferred embodiments the label is selected from the group consisting of a fluorescent protein and an enzyme.

According to an additional aspect of the present invention there is provided a method of producing an antibody specifically bindable with a binding affinity below 20 nanomolar to a human major histocompatibility complex (MHC) class I being complexed with a HLA-restricted antigen, the method comprising: immunizing a genetically engineered non-human mammal having cells expressing the human major histocompatibility complex (MHC) class I with a soluble form of a MHC class I molecule being complexed with the HLA-restricted antigen; isolating mRNA molecules from antibody producing cells of the non-human mammal; producing a phage display library displaying protein molecules encoded by the mRNA molecules; and isolating at least one phage from the phage display library, the at least one phage displaying the antibody specifically bindable with the affinity below 10 nanomolar to the human major histocompatibility complex (MHC) class I being complexed with the HLA-restricted antigen.

According to still further features in the described preferred embodiments the non-human mammal is devoid of self MHC class I molecules.

According to still further features in the described preferred embodiments the HLA-restricted antigen is a tumor HLA-restricted antigen.

According to still further features in the described preferred embodiments the HLA-restricted antigen is a viral HLA-restricted antigen.

According to still further features in the described preferred embodiments the HLA-restricted antigen is an autoimmune HLA-restricted antigen.

According to still further features in the described preferred embodiments the soluble form of a MHC class I molecule is a single chain MHC class I polypeptide including a functional human β-2 microglobulin amino acid sequence directly or indirectly covalently linked to a functional human MHC class I heavy chain amino acid sequence.

According to still an additional aspect of the present invention there is provided a method of treating a cancer, the method comprising administering to a subject in need thereof a therapeutically effective amount of a molecule which comprises an antibody specifically bindable with a binding affinity below 20 nanomolar to a human major histocompatibility complex (MHC) class I being complexed with a tumor HLA-restricted antigen characterizing the cancer, the molecule further comprises a therapeutic moiety being conjugated to the antibody, the MHC class I molecule being selected matching to the endogenous MHC class I of the subject.

According to yet an additional aspect of the present invention there is provided a method of treating a viral infection, the method comprising administering to a subject in need thereof a therapeutically effective amount of a molecule which comprises an antibody specifically bindable with a binding affinity below 20 nanomolar to a human major histocompatibility complex (MHC) class I being complexed with a viral HLA-restricted antigen characterizing a virus causative of the viral infection, the molecule further comprises a therapeutic moiety being conjugated to the antibody, the MHC class I molecule being selected matching to the endogenous MHC class I of the subject.

According to yet an additional aspect of the present invention there is provided a method of treating an autoimmune disease, the method comprising administering to a subject in need thereof a therapeutically effective amount of a molecule which comprises an antibody specifically bindable with a binding affinity below 20 nanomolar to a human major histocompatibility complex (MHC) class I being complexed with an autoimmune HLA-restricted antigen, the molecule further comprises a therapeutic moiety being conjugated to the antibody, the MHC class I molecule being selected matching to the endogenous MHC class I of the subject.

According to further features in preferred embodiments of the invention described below, the MHC class I molecule is selected from the group consisting of HLA-A2, HLA-A1, HLA-A3, HLA-A24, HLA-A28, HLA-A31, HLA-A33, HLA-A34, HLA-B7, HLA-B45 and HLA-Cw8.

According to still further features in the described preferred embodiments the therapeutic moiety is selected from the group consisting of a cytotoxic moiety, a toxic moiety, a cytokine moiety and a bi-specific antibody moiety.

According to another aspect of the present invention there is provided a method of making an immunotoxin, the method comprising ligating a first polynucleotide encoding an antibody specifically bindable with a binding affinity below 20 nanomolar to a human major histocompatibility complex (MHC) class I being complexed with a HLA-restricted antigen in frame with a second polynucleotide encoding a toxin moiety, so a to obtain a ligated polynucleotide and expressing the ligated polynucleotide in an expression system so as to obtain the immunotoxin.

According to another aspect of the present invention there is provided a method of making an immunolabel, the method comprising ligating a first polynucleotide encoding an antibody specifically bindable with a binding affinity below 20 nanomolar to a human major histocompatibility complex (MHC) class I being complexed with a HLA-restricted antigen in frame with a second polynucleotide encoding an identifiable moiety, so a to obtain a ligated polynucleotide and expressing the ligated polynucleotide in an expression system so as to obtain the immunolabel.

According to another aspect of the present invention there is provided a method of detecting the presence and/or level of antigen presenting cells presenting a HLA-restricted antigen in a sample of cells, the method comprising interacting cells of the sample with an antibody specifically bindable with a binding affinity below 20 nanomolar to a human major histocompatibility complex (MHC) class I being complexed with a HLA-restricted antigen; and monitoring the interaction, thereby detecting the presence and/or level of the antigen presenting cells presenting the HLA-restricted antigen.

Depending on the application, the HLA-restricted antigen is selected from the group consisting of a tumor HLA-restricted antigen, a viral HLA-restricted antigen and an autoimmune HLA-restricted antigen.

The present invention successfully addresses the shortcomings of the presently known configurations by providing an antibody having a T-cell receptor specificity and high affinity to its antigen, and the use thereof in immunotherapy and immunodiagnosis.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A–B show bar graphs demonstrating polyclonal phage ELISA on recombinant scHLA-A2-peptide complexes. Plates were coated with the indicated scMHC-peptide complex as described in the Examples section that follows. Shown is the binding of the polyclonal phage population of the initial library (L) or phages eluted after each round of panning (I-IV). FIG. 1A—phages from the pCANTAB scFv library; FIG. 1B—phages from the scFv-CBD library. Binding specificity studies were performed by ELISA using biotinylated scMHC-peptide complexes. ELISA plates (Falcon) were coated overnight with BSA-biotin (1 $\mu$g/well), washed, incubated (1 hr, RT) with streptavidin (1 $\mu$g/well), washed again extensively and further incubated (1 hr, RT) with 0.5 $\mu$g of MHC/peptide complexes. Plates were blocked with PBS/2% milk (30 min, RT), incubated with phage clones (~$10^9$ phages/well, 1 hr, RT) or 0.5–1 $\mu$g of soluble scFv or scFv-PE38, and afterwards washed with 1:1000 HRP-conjugated/anti-M13, anti-myc antibody or anti-PE antibody, respectively. The HLA-A2-restricted peptides used for specificity studies are gp100 (154): KTWGQYWQV (SEQ ID NO:1); gp100 (209): IMDQVPFSV (SEQ ID NO:2); gp100 (280): YLEPGPVTV (SEQ ID NO:3); MUC1: LLLTVLTVL (SEQ ID NO:4); HTLV-1 (TAX): LLFGYPVYV (SEQ ID NO:5); hTERT (540): ILAKFLHWL (SEQ ID NO:6); hTERT (865): RLVDDFLLV (SEQ ID NO:7).

FIGS. 2A–B show bar graphs demonstrating differential binding of monoclonal phage clones to scHLA-A2/gp100 complexes. Monoclonal phage were tested for binding to immobilized scHLA-A2 complexed with the gp100-derived epitopes. FIG. 2A—G9-209M; FIG. 2B—G9-280V. The assays were performed similar to as described under FIG. 1 above.

FIG. 3A shows the nucleic (SEQ ID NO:8) and amino (SEQ ID NO:9) acid sequences of the antibody G1 scFv. CDRs are marked in bold, the peptide linker connecting the VH and VL domains is underlined.

FIGS. 3B–C show SDS-PAGE analysis of purified G1scFv and G1scFv-PE38. The G1 scFv gene was rescued from the phage clone by PCR and was subcloned into the phagemid vector pCANTAB6 via the SfiI-NotI cloning sites. A Myc and hexahistidine tags were fused to the C-terminus of the scFv gene. The scFv antibody was expressed in BL21 λDE3 cells as previously described (29) and purified from the periplasmic fraction by metal-ion affinity chromatography. For the expression of the G1scFv-PE38 fusion protein, the scFv gene was subcloned as an NcoI-NotI fragment into the plasmid pIB-NN, which encodes the translocation and ADP-ribosylation domains of PE (PE38). Expression in BL21 λDE3 cells, refolding from inclusion bodies, and purification of G1scFv-PE38 was performed as previously described (30).

FIG. 4 is a bar graph demonstrating the binding specificity of G1 scFv-PE38. Immunoplates were coated with various indicated scHLA-A2-peptide complexes as described and binding of the G1 scFv-PE38 to immobilized complexes was detected with anti-PE antibodies.

FIGS. 5A–B show plots demonstrating the binding characteristics of the TCR-like G1 scFv. 5A—Titration ELISA of purified soluble G1 scFv. Wells were coated with the MHC-peptide complexes as described in the Examples section that follows. 5B—Competitive binding analysis of the ability of purified G1 scFv-PE38 to inhibit the binding of 125I-labeled G1 scFv-PE38 to the HLA-A2/G9-209M complex. The apparent binding affinity of the recombinant scFv was determined as the concentration of competitor (soluble purified G1scFv-PE38) required for 50% inhibition of the binding of the $^{125}$I-labeled tracer. Flexible ELISA plates were coated with BSA-biotin and scMHC-peptide complexes (10 $\mu$g in 100 $\mu$l) were immobilized as previously described. The recombinant G1scFv-PE38 was labeled with [$^{125}$I] using the Bolton-Hunter reagent. Labeled protein was added to wells as a tracer (3–5×$10^5$ CPM/well) in the presence of increasing concentrations of cold G1scFv-PE38 as a competitor and incubated at room temperature for 1 hr in PBS. The plates were washed thoroughly with PBS and the bound radioactivity was determined by a gamma counter. The apparent affinity of the G1scFv-PE38 was determined by extrapolating the concentration of a competitor necessary to achieve 50% inhibition of [$^{125}$I]-labeled G1scFv-PE38 binding to the immobilized scMHC-peptide complex. Non-specific binding was determined by adding a 20–40-fold excess of unlabeled Fab.

Figure 6A:
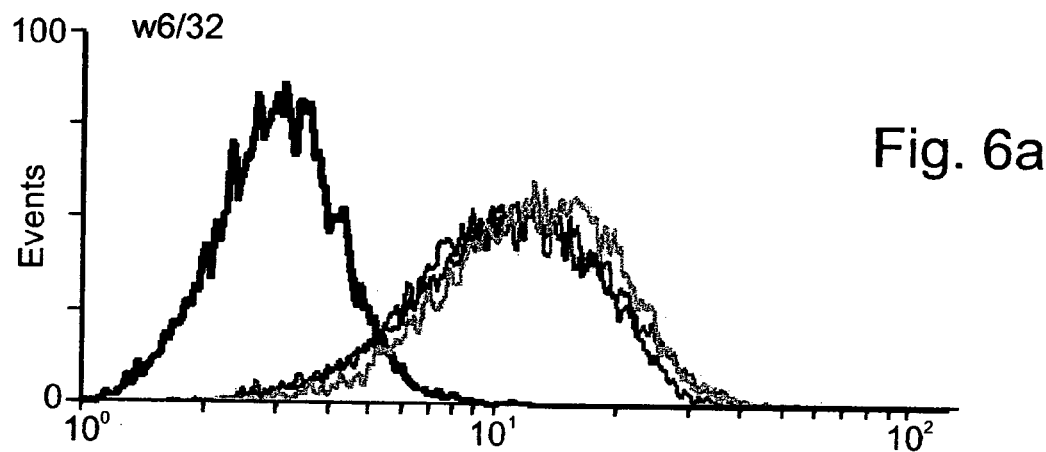
Figure 6B:
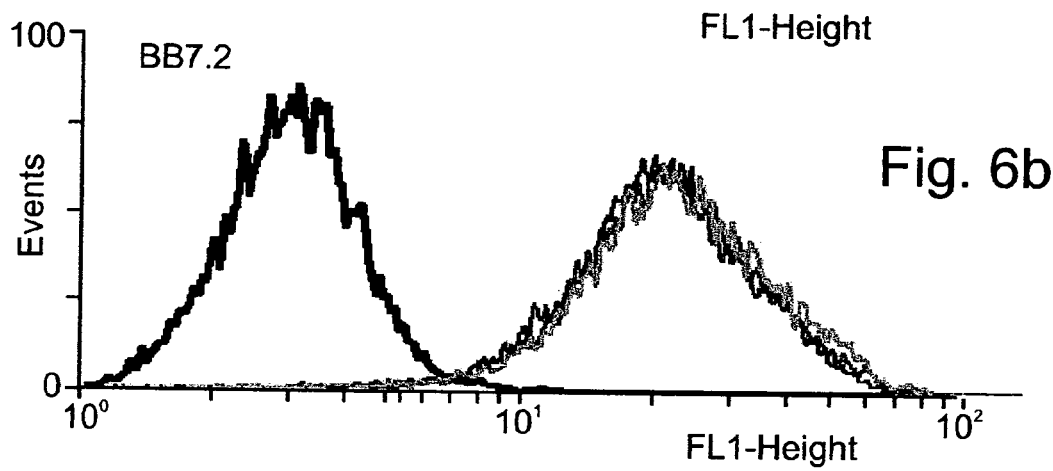
Figure 6C:
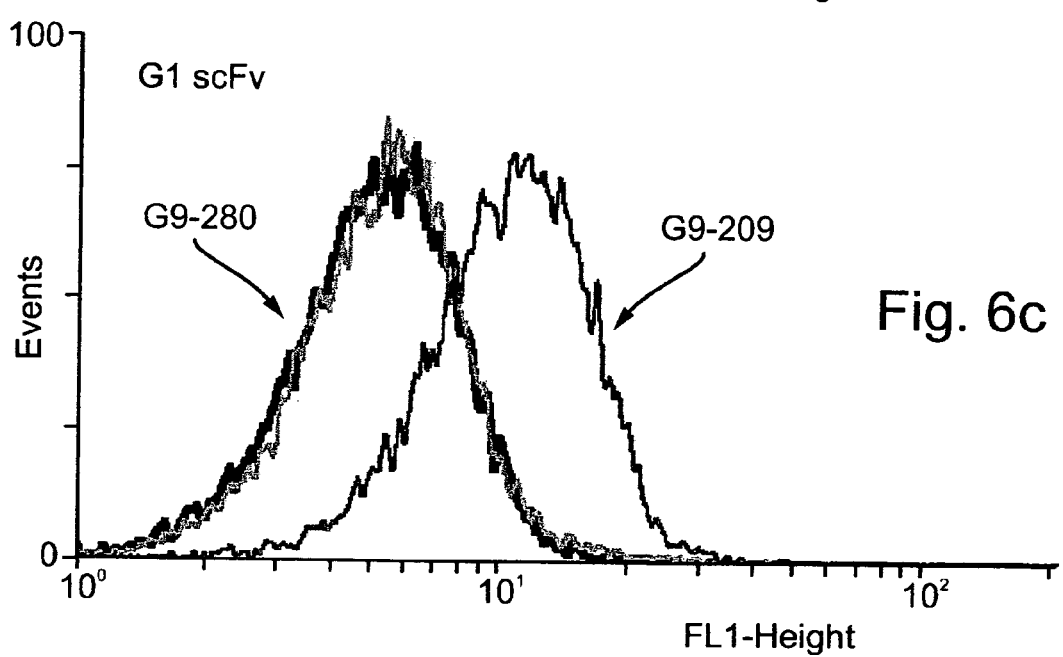

FIGS. 6A–C show plots demonstrating the binding of G1 scFv to APCs. RMAS-HHD or JY cells were loaded with the indicated HLA-A2-restricted peptides. Peptide loaded cells were then incubated with the soluble purified G1 scFv antibody. Detection of binding was with FITC-labeled anti-Myc. RMAS-HHD cells loaded with the G9-209 and G9-280 peptides and stained together with control unloaded cells the anti-HLA antibody w6/32 (6A) or anti-HLA-A2 antibody BB7.2 (6B) to demonstrate the stabilization/expression of HLA-A2 complexes on the surface of peptide loaded but not on peptide-unloaded cells. Cells loaded with G9-209 or G9-280 peptides were stained with G1 scFv and the differential staining is shown (6C). The B cell line RMAS-HHD transfected with a single-chain β2M-HLA-A2 gene (26) or the EBV-transformed B-lymphoblast JY cells ($10^6$ cells) were washed twice with serum-free RPMI and incubated overnight at 26° C. or 37° C., respectively, in medium containing 100 μM of the peptide. The APCs were subsequently incubated at 37° C. for 2–3 hours to stabilize cell surface expression of MHC-peptide complexes followed by incubation with recombinant scFv (10–50 μg/ml, 60–90 minutes, 4° C.) in 100 μl. The cells were then washed, incubated with FITC-labeled anti-Myc antibody (30–45 minutes, 4° C.), and finally washed and analyzed by a FACStar flow cytometer (Becton Dickinson). Melanoma cells were pulsed at 37° C. with 1–10 μM of peptide and then stained with the scFv as described herein.

Figure 7A:
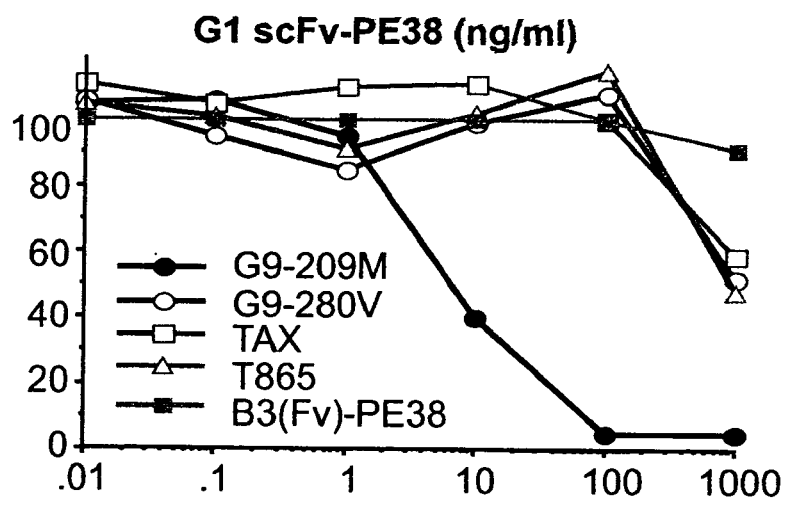
Figure 7B:
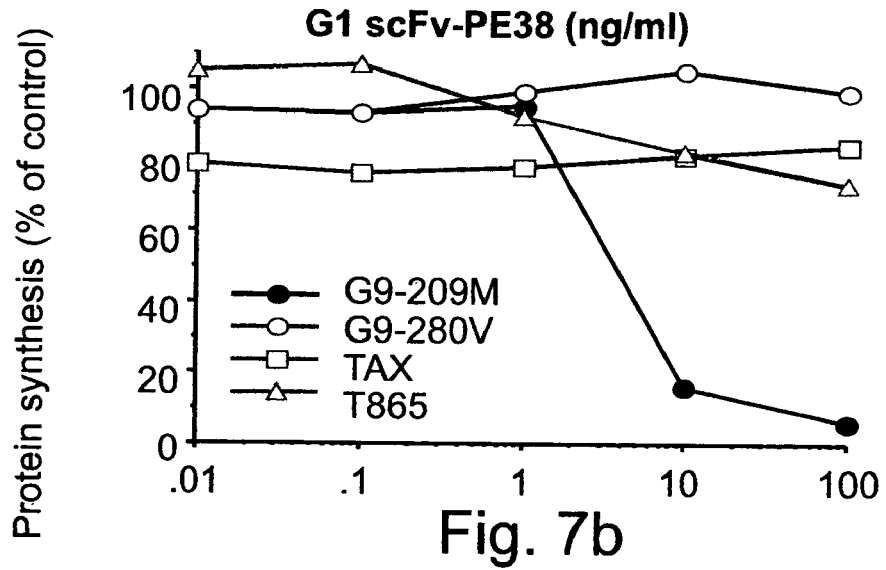
Figure 7C:
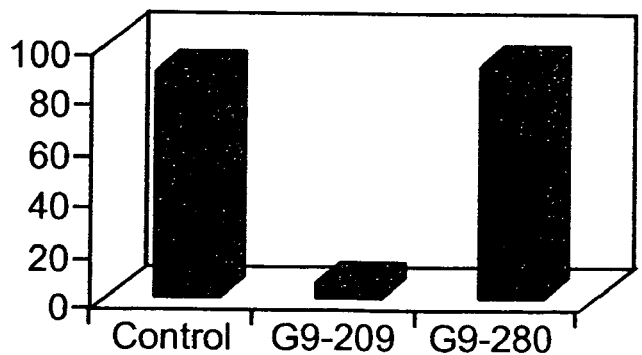

FIGS. 7A–C show plots and a bar graph demonstrating the cytotoxic activity of G1 scFv-PE38 on peptide-loaded APCs. RMAS-HHD (7A) or JY (7B) cells were loaded with the HLA-A2-restricted peptides as indicated, followed by incubation with increasing concentrations of G1 scFv-PE38. Protein synthesis was determined by incorporation of $^3$H-Leucine into cellular proteins. In (7C) excess (0.15–0.25 mg/ml) of the indicated scHLA-A2-peptide complex was added to the wells before the addition of G1 scFv-PE38 (25–50 ng/ml). RMAS-HHD and JY APCs were loaded with the G9-209 peptide and control peptides as described above. Peptide-loaded cells were subsequently incubated with increasing concentrations of G1scFv-PE38 and the inhibition of protein synthesis was determined by measuring the uptake of $^3$H-Leucine into cellular proteins, as previously described (30). $IC_{50}$ was determined as the concentration of G1scFv-PE38 required to inhibit protein synthesis by 50%. In competition assays, excesses of specific and non-specific HLA-A2-peptide complexes (35–50 μg/well) were added to wells 15 minutes before the addition of G 1 scFv-PE38.

DESCRIPTION OF THE PREFERRED EMBODIMENTS

The present invention is of an antibody having a T-cell receptor specificity yet far higher affinity, conjugates of same with identifiable and/or therapeutic moieties, so as to generate immunotoxins and immunolabels, method of making the antibody and the conjugates, polynucleotides encoding the antibody and the conjugates and methods of using the conjugates in the detection and treatment of cancer, viral infection and autoimmune disease.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The immune system is controlled and regulated by the T-cell receptor (TCR), which specifically recognizes peptide/Major histocompatibility complex (MHC) molecules.

The advent of the application of recombinant class I MHC-peptide complexes and their tetrameric arrays now enables to detect and study rare populations of antigen-specific T cells (25, 35, 36). However, fundamental questions in immunology in general, and in tumor immunology in particular, regarding antigen presentation are still open because of the lack of reagents that will enable phenotypic analysis of antigen (MHC-peptide) presentation, the other side of the coin to MHC-peptide-TCR interactions. One way to generate such reagents is by making TCR-like antibodies; however, only a few publications have reported the generation of self-MHC-restricted antibodies by conventional means such as the hybridoma technology (13–16). The major reason for these past difficulties may be found in the molecular nature and the resolved structures of MHC-peptide complexes. More specifically, the peptides are deeply buried inside the MHC-binding groove and therefore they are presented as extended mosaics of peptide residues intermingled with the MHC residues. It has been shown that no more than 100–300 Å$^2$ of class I MHC-bound peptide faces outwards and thus is available for direct recognition, whereas antibodies recognizing protein molecules engage about 800 Å$^2$ of their ligand (17). Thus, when generating TCR-like antibodies, these molecules will presumably recognize the peptide but will also have to be dominated by the MHC.

Until now, antibodies with TCR-like specificity have been generated against murine MHC-peptide complexes employing various strategies of immunization (17). Recently, a large human Fab library was used to select for HLA-A1-MAGE-A1-specific binding antibodies (18). One specific clone, G8, was selected which exhibited TCR-like specificity but revealed a relatively low affinity of 250 nM.

While reducing the present invention to practice, the ability to select from an immune repertoire of murine scFv fragments a high affinity antibody directed toward a human T-cell epitope was demonstrated.

According to an aspect of the present invention there is provided a method of producing an antibody specifically bindable with a binding affinity below 20 nanomolar to a human major histocompatibility complex (MHC) class I which is complexed with a HLA-restricted antigen. The method according to this aspect of the invention is effected by (i) immunizing a genetically engineered non-human mammal having cells expressing the human major histocompatibility complex (MHC) class I, with a soluble form of a MHC class I molecule being complexed with the HLA-restricted antigen; (ii) isolating mRNA molecules from antibody producing cells, such as splenocytes, of the non-human mammal; (iii) producing a phage display library displaying protein molecules encoded by the mRNA molecules; and (iv) isolating at least one phage from the phage display library, the at least one phage displaying the antibody specifically bindable with the affinity below 10 nanomolar to the human major histocompatibility complex (MHC) class I being complexed with the HLA-restricted antigen. The genetic material of the phage isolate is then used to prepare a single chain antibody or other forms of antibodies as is further described herein below. The genetic material of the phage isolate is then used to prepare a single chain antibody or other forms of antibodies as is further described hereinbelow and which are conjugated to identifiable or therapeutic moieties. Preferably, the non-human mammal is devoid of self MHC class I molecules. Still preferably, the soluble form of a MHC class I molecule is a single chain MHC class I polypeptide including a functional human β-2 microglobulin amino acid sequence directly or indirectly covalently linked to a functional human MHC class I heavy chain amino acid sequence.

Hence, according to another aspect of the present invention there is provided an isolated molecule comprising an antibody specifically bindable with a binding affinity below 20 nanomolar to a human major histocompatibility complex (MHC) class I complexed with a HLA-restricted antigen. Such an antibody has a T-cell receptor specificity, yet far higher affinity. In one, non-limiting example, the antibody is a single chain antibody having an amino acid sequence as set forth in SEQ ID NO:9, encoded, for example, by the polynucleotide as set forth in SEQ ID NO:8.

Once a polynucleotide encoding an antibody having a T-cell receptor specificity as herein described is cloned, it can be modified in one of many ways in order to produce a spectrum of related-products.

In one example, the polynucleotide encoding an antibody having a T-cell receptor specificity is ligated with a second polynucleotide encoding an identifiable moiety, so as to produce an antibody having a T-cell receptor specificity conjugated to the identifiable moiety, an immunolabel. Such a conjugate or immunolabel can be used in a method of detecting the presence and/or level of antigen presenting cells presenting a HLA-restricted antigen in a sample of cells and serve for diagnosis of cancer, viral infection or autoimmune disease. As used herein, the phrase "antigen presenting cell" includes all cells expressing MHC, class I molecules on their surface, and which are capable of presenting HLA-restricted antigens. An antigen presenting cell can be a cancer cell, a cell of the immune system, or any other cell expressing MHC, class I molecules on its surface.

Hence, according to another aspect of the present invention there is provided a method of making an immunolabel, the method comprising ligating a first polynucleotide encoding an antibody specifically bindable with a binding affinity below 20 nanomolar to a human major histocompatibility complex (MHC) class I being complexed with a HLA-restricted antigen in frame with a second polynucleotide encoding an identifiable moiety, so a to obtain a ligated polynucleotide and expressing the ligated polynucleotide in an expression system so as to obtain the immunolabel.

And, according to yet another aspect of the present invention there is provided a method of detecting the presence and/or level of antigen presenting cells presenting a HLA-restricted antigen in a sample of cells, the method comprising interacting cells of said sample with an antibody specifically bindable with a binding affinity below 20 nanomolar to a human major histocompatibility complex (MHC) class I being complexed with a HLA-restricted antigen; and monitoring said interaction, thereby detecting the presence and/or level of said antigen presenting cells presenting said HLA-restricted antigen.

Depending on the application, the HLA-restricted antigen can be a tumor HLA-restricted antigen, a viral HLA-restricted antigen and an autoimmune HLA-restricted antigen, examples of which are provided hereinbelow.

According to yet another aspect of the present invention there is provided a diagnostic composition comprising a molecule which comprises an antibody specifically bindable with a binding affinity below 20 nanomolar to a human major histocompatibility complex (MHC) class I being complexed with a HLA-restricted antigen, the molecule further comprises an identifiable moiety being conjugated to the antibody.

The identifiable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

In another example, the polynucleotide encoding an antibody having a T-cell receptor specificity is ligated with a second polynucleotide encoding a therapeutic moiety, so as to produce an antibody having a T-cell receptor specificity conjugated to the therapeutic moiety. Such a conjugate or immunotoxin can be used in a method of treating cancer, viral infection or autoimmune disease.

Hence, according to another aspect of the present invention there is provided a method of making an immunotoxin, the method comprising ligating a first polynucleotide encoding an antibody specifically bindable with a binding affinity below 20 nanomolar to a human major histocompatibility complex (MHC) class I being complexed with a HLA-restricted antigen in frame with a second polynucleotide encoding a toxin moiety, so a to obtain a ligated polynucleotide and expressing said ligated polynucleotide in an expression system so as to obtain said immunotoxin.

The immunotoxin can be used in any one of the following therapeutic protocols:

(i) A method of treating a cancer, the method comprising administering to a subject in need thereof a therapeutically effective amount of a molecule which comprises an antibody specifically bindable with a binding affinity below 20 nanomolar to a human major histocompatibility complex (MHC) class I being complexed with a tumor HLA-restricted antigen characterizing the cancer, the molecule further comprises a therapeutic moiety being conjugated to the antibody, the MHC class I molecule being selected matching to the endogenous MHC class I of the subject.

(ii) A method of treating a viral infection, the method comprising administering to a subject in need thereof a therapeutically effective amount of a molecule which comprises an antibody specifically bindable with a binding affinity below 20 nanomolar to a human major histocompatibility complex (MHC) class I being complexed with a viral HLA-restricted antigen characterizing a virus causative of the viral infection, the molecule further comprises a therapeutic moiety being conjugated to the antibody, the MHC class I molecule being selected matching to the endogenous MHC class I of the subject.

(iii) A method of treating an autoimmune disease, the method comprising administering to a subject in need thereof a therapeutically effective amount of a molecule which comprises an antibody specifically bindable with a binding affinity below 20 nanomolar to a human major histocompatibility complex (MHC) class I being complexed with an autoimmune HLA-restricted antigen, said molecule further comprises a therapeutic moiety being conjugated to said antibody, said MHC class I molecule being selected matching to the endogenous MHC class I of the subject.

According to another aspect of the present invention there is provided a pharmaceutical composition comprising a therapeutically effective amount of a molecule which comprises an antibody specifically bindable with a binding affinity below 20 nanomolar to a human major histocompatibility complex (MHC) class I being complexed with a HLA-restricted antigen, the molecule further comprises a therapeutic moiety being conjugated to the antibody. Preferably, the pharmaceutical composition further comprising a pharmaceutically acceptable carrier.

The therapeutic moiety can be, for example, a cytotoxic moiety, a toxic moiety, a cytokine moiety and a bi-specific antibody moiety, examples of which are provided hereinbelow.

In all applications the MHC class I can be, for example, HLA-A2, HLA-A1, HLA-A3, HLA-A24, HLA-A28, HLA-A31, HLA-A33, HLA-A34, HLA-B7, HLA-B45 and HLA-Cw8.

The following sections provide specific examples and alternatives for each of the various aspects of the invention described herein. These examples and alternatives should not be regarded as limiting in any way, as the invention can be practiced in similar, yet somewhat different ways. These examples, however, teach one of ordinary skills in the art how to practice various alternatives and embodiments of the invention.

Antibody:

The term "antibody" as used to describe this invention includes intact molecules as well as functional fragments thereof, such as Fab, F(ab')$_2$, Fv and scFv that are capable of specific, high affinity binding to a human major histocompatibility complex (MHC) class I complexed with a HLA-restricted antigen. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (c) scFv or "single chain antibody" ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119–126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659–62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97–105, 1991; Bird et al., Science 242:423–426, 1988; Pack et al., Bio/Technology 11:1271–77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106–10, 1991.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522–525 (1986); Riechmann et al., Nature 332:323–327 (1988); Verhoeyen et al., Science, 239:1534–1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368 812–13 (1994); Fishwild et al., Nature Biotechnology 14, 845–51 (1996); Neuberger, Nature Biotechnology 14, 826 (1996); Lonberg and Huszar, Intern. Rev. Immunol. 13 65–93 (1995).

It will be appreciated that once the CDRs of an antibody are identified, using conventional genetic engineering techniques can be used to devise expressible polynucleotides encoding any of the forms or fragments of antibodies described herein.

A Human Major Histocompatibility Complex (MHC) Class I:

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

Major histocompatibility complex (MHC) class I molecules are expressed on the surface of nearly all cells. These molecules function in presenting peptides which are mainly derived from endogenously synthesized proteins to CD8+ T cells via an interaction with the αβ T-cell receptor. The class I MHC molecule is a heterodimer composed of a 46-kDa heavy chain which is non-covalently associated with the 12-kDa light chain β2 microglobulin. In humans, there are several MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, their sequences can be found at the kabat data base, at immuno.bme.nwu.edu/, which is incorporated herein by reference.

Peptides that Bind to Class I MHC Molecules; HLA-Restricted Antigens:

Class I, MHC-restricted peptides (also referred to herein interchangeably as HLA-restricted antigens, HLA-restricted peptides, MHC-restricted antigens) which are typically 8–10-amino acid-long, bind to the heavy chain o1–o2 groove via two or three anchor residues that interact with corresponding binding pockets in the MHC molecule. The β2 microglobulin chain plays an important role in MHC class I intracellular transport, peptide binding, and conformational stability. For most class I molecules, the formation of a heterodimer consisting of the MHC class I heavy chain, peptide (self or antigenic) and β-2 microglobulin is required for biosynthetic maturation and cell-surface expression.

Research studies performed on peptide binding to class I MHC molecules enable to define specific MHC motifs functional in displaying peptides derived from viral, tumor and self antigens that are potentially immunogenic and might elicit specific response from cytotoxic T lymphocytes (CTLs).

As used herein the term "peptide" refers to native peptides (either degradation products or synthetically synthesized peptides) and further to peptidomimetics, such as peptoids and semipeptoids which are peptide analogs, which may have, for example, modifications rendering the peptides more stable while in a body, or more immunogenic. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein. Further detail in this respect are provided hereinunder.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids useful in MHC-I HLA-A2 recognizable peptide antigens are given hereinunder.

Based on accumulated experimental data, it is nowadays possible to predict which of the peptides of a protein will bind to MHC, class I. The HLA-A2 MHC class I has been so far characterized better than other HLA haplotypes, yet predictive and/or sporadic data is available for all other haplotypes.

With respect to HLA-A2 binding peptides, assume the following positions (P1–P9) in a 9-mer peptide:

P1–P2–P3–P4–P5–P6–P7–P8–P9

The P2 and P2 positions include the anchor residues which are the main residues participating in binding to MHC molecules. Amino acid resides engaging positions P2 and P9 are hydrophilic aliphatic non-charged natural amino (examples being Ala, Val, Leu, Ile, Gln, Thr, Ser, Cys, preferably Val and Leu) or of a non-natural hydrophilic aliphatic non-charged amino acid (examples being norleucine (Nle), norvaline (Nva), α-aminobutyric acid). Positions P1 and P3 are also known to include amino acid residues which participate or assist in binding to MHC molecules, however, these positions can include any amino acids, natural or non-natural. The other positions are engaged by amino acid residues which typically do not participate in binding, rather these amino acids are presented to the immune cells. Further details relating to the binding of peptides to MHC molecules can be found in Parker, K. C., Bednarek, M. A., Coligan, J. E., Scheme for ranking potential HLA-A2 binding peptides based on independent binding of individual peptide side-chains. J. Immunol.152,163–175,1994., see Table V, in particular. Hence, scoring of HLA-A2.1 binding peptides can be performed using the HLA Peptide Binding Predictions software approachable through a worldwide web interface at bimas.dcrt.nih.gov/molbio/hla_bind/index.html. This software is based on accumulated data and scores every possible peptide in an analyzed protein for possible binding to MHC HLA-A2.1 according to the contribution of every amino acid in the peptide. Theoretical binding scores represent calculated half-life of the HLA-A2.1-peptide complex.

Hydrophilic aliphatic natural amino acids at P2 and P9 can be substituted by synthetic amino acids, preferably Nleu, Nval and/or α-aminobutyric acid. P9 can be also substituted by aliphatic amino acids of the general formula —HN(CH$_2$)$_n$COOH, wherein n=3–5, as well as by branched derivatives thereof, such as, but not limited to,

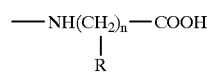

wherein R is, for example, methyl, ethyl or propyl, located at any one or more of the n carbons.

The amino terminal residue (position P1) can be substituted by positively charged aliphatic carboxylic acids, such as, but not limited to, H$_2$N(CH$_2$)$_n$COOH, wherein n=2–4 and H$_2$N—C(NH)—NH(CH$_2$)$_n$COOH, wherein n=2–3, as well as by hydroxy Lysine, N-methyl Lysine or ornithine (Orn). Additionally, the amino terminal residue can be substituted by enlarged aromatic residues, such as, but not limited to, H$_2$N—(C$_6$H$_6$)—CH$_2$—COOH, p-aminophenyl alanine, H$_2$N—F(NH)—NH—(C$_6$H$_6$)—CH$_2$—COOH, p-guanidinophenyl alanine or pyridinoalanine (Pal). These latter residues may form hydrogen bonding with the OH$^-$ moieties of the Tyrosine residues at the MHC-1 N-terminal binding pocket, as well as to create, at the same time aromatic—aromatic interactions.

Derivatization of amino acid residues at positions P4–P8, should these residues have a side-chain, such as, OH, SH or NH$_2$, like Ser, Tyr, Lys, Cys or Orn, can be by alkyl, aryl, alkanoyl or aroyl. In addition, OH groups at these positions may also be derivatized by phosphorylation and/or glycosylation. These derivatizations have been shown in some cases to enhance the binding to the T cell receptor.

Longer derivatives in which the second anchor amino acid is at position P10 may include at P9 most L amino acids. In some cases shorter derivatives are also applicable, in which the C terminal acid serves as the second anchor residue.

Cyclic amino acid derivatives can engage position P4–P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—COOH)—C(R)H—NH$_2$, wherein n=1–4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—CH$_2$—)$_n$—S—CH$_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom.

These modifications can occur at any of the bonds along the peptide chain and even at several (2–3) at the same time. Preferably, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Tumor HLA-Restricted Antigens:

The references recited in the following Table provide examples of human MHC class I, tumor HLA-restricted peptides derived from tumor associated antigens (TAA) or protein markers associated with various cancers. Additional tumor HLA-restricted peptides derived from tumor associated antigens (TAA) can be found in bmi-heidelberg.com/syfpeithi/

| Cancer | TAA/Marker | HLA | Reference |
|---|---|---|---|
| Transitional cell carcinoma | Uroplakin II | HLA-A2 | WO 00/06723 |
| Transitional cell carcinoma | Uroplakin Ia | HLA-A2 | WO 00/06723 |
| Carcinoma of the prostate | prostate specific antigen | HLA-A2 | WO 00/06723 |
| Carcinoma of the prostate | prostate specific membrane antigen | HLA-A2 | WO 00/06723 |
| Carcinoma of the prostate | prostate acid phosphatase | HLA-A2 | WO 00/06723 |
| Breast cancer | BA-46 | HLA-A2 | WO 00/06723 |
| Breast cancer | Muc-1 | HLA-A2 | WO 00/06723 |

-continued

| Cancer | TAA/Marker | HLA | Reference |
|---|---|---|---|
| Melanoma | Gp100 | HLA-A2 | Reference 54 |
| Melanoma | MART1 | HLA-A2 | Reference 54 |
| All tumors | Telomerase | HLA-A2 | Reference 54 |
| Leukemia | TAX | HLA-A2 | Reference 54 |
| Carcinomas | NY-ESO | HLA-A2 | Reference 54 |
| Melanoma | MAGE-A1 | HLA-A2 | Reference 54 |
| Melanoma | MAGE-A3 | HLA-A24 | Reference 54 |
| Carcinomas | HER2 | HLA-A2 | Reference 54 |
| Melanoma | Beta-catenine | HLA-A24 | Reference 54 |
| Melanoma | Tyrosinase | HLA-DRB1 | Reference 54 |
| Leukemia | Bcr-abl | HLA-A2 | Reference 54 |
| Head and neck | Caspase 8 | HLA-B35 | Reference 54 |

Viral HLA-Restricted Antigens:

The references recited in the following Table provide examples of human MHC class I, viral HLA-restricted peptides derived from viral antigens associated with various cancers.

| Disease | Viral antigen | HLA | Reference |
|---|---|---|---|
| AIDS (HTLV-1) | HIV-1 RT 476-484 | HLA-A2 | bmi-heidelberg.com/syfpeithi/ |
| Influenza | G I L G F V F T L (SEQ ID NO:10) | HLA-A2 | bmi-heidelberg.com/syfpeithi/ |
| CMV disease | CMV | HLA-A2 | bmi-heidelberg.com/syfpeithi/ |
| Burkitts Lymphoma | TAX | HLA-A2 | bmi-heidelberg.com/syfpeithi/ |
| Hepatitis C | HCV | HLA-A2 | bmi-heidelberg.com/syfpeithi/ |
| Hepatitis B | HBV pre-S protein 85–66 S T N R Q S G R Q (SEQ ID NO:11) | HLA-A2 | bmi-heidelberg.com/syfpeithi/ |
| HTLV-1 Leukemia | HTLV-1 tax 11–19 | HLA-A2 | bmi-heidelberg.com/syfpeithi/ |
| Hepatitis | HBV surface antigen 185–194 | HLA-A2 | bmi-heidelberg.com/syfpeithi/ |

Autoimmune HLA-Restricted Antigens:

The website bmi-heidelberg.com/syfpeithi/provides 5examples of human MHC class I, autoimmune HLA-restricted peptides derived from autoimmune antigens.

Soluble MHC class I Molecules:

Recombinant MHC class I and class II complexes which are soluble and which can be produced in large quantities are described in, for example, references 23, 24 and 41–53 and further in U.S. patent application Ser. No. 09/534,966 and PCT/IL01/00260 (published as WO 01/72768), all of which are incorporated herein by reference. Soluble MHC class I molecules are available or can be produced for any of the MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, following, for example the teachings of PCT/IL01/00260, as their sequences are known and can be found at the kabat data base, at immuno.bme.nwu.edu/, the contents of the site is incorporated herein by reference. Such soluble MHC class I molecules can be loaded with suitable HLA-restricted antigens and used for vaccination of Non-human mammal having cells expressing the human major histocompatibility complex (MHC) class I as is further detailed herein below.

Non-Human Mammal Having Cells Expressing the Human Major Histocompatibility Complex (MHC) Class I:

Non-human mammal having cells expressing a human major histocompatibility complex (MHC) class I and devoid of self major histocompatibility complex (MHC) class I can be produced using (i) the sequence information provided in the kabbat data base, at immuno.bme.nwu.edu/, which is incorporated herein by reference and pertaining to human MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, (ii) conventional constructs preparation techniques, as described in, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); and (iii) conventional gene knock-in/knock-out techniques as set forth, for example, in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866; in International Publications WO 94/23049, WO93/14200, WO 94/06908 and WO 94/28123; as well as in Burke and Olson, Methods in Enzymology, 194:251–270, 1991; Capecchi, Science 244:1288–1292, 1989; Davies et al., Nucleic Acids Research, 20 (11) 2693–2698, 1992; Dickinson et al., Human Molecular Genetics, 2(8): 1299–1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742–750 1991; Jakobovits et al., Nature, 362:255–261, 1993; Lamb et al., Nature Genetics, 5: 22–29, 1993; Pearson and Choi, Proc. Natl. Acad. Sci. USA, 1993. 90:10578–82; Rothstein, Methods in Enzymology, 194:281–301, 1991; Schedl et al., Nature, 362: 258–261, 1993; Strauss et al., Science, 259:1904–1907, 1993, all of which are incorporated herein by reference.

Of particular interest is the paper by Pascolo et al., published in J. Exp. Med. 185: 2043–2051, 1997, which describe the preparation of mice expressing the human HLA-A2.1, H-2 Db and HHD MHC class I molecules and devoid of mice MHC class I altogether.

Identifiable Moieties:

In some aspects thereof, the present invention employ conjugates of an antibody and an identifiable moiety. To this end, in one example, first and second polynucleotides encoding the antibody and the identifiable moiety, respectively, are ligated in frame, so as to encode an immunolabel. The following table provide examples of sequences of identifiable moieties.

| Identifiable Moiety | Amino Acid sequence (Genebank Accession No.) | Nucleic Acid sequence (Genebank Accession No.) |
|---|---|---|
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |
| orange fluorescent protein | AAL33917 | AF435432 |
| Beta galactosidase | NM_125776 | NM_125776 |

-continued

| Identifiable Moiety | Amino Acid sequence (Genebank Accession No.) | Nucleic Acid sequence (Genebank Accession No.) |
|---|---|---|
| Fluorescein isothiocyanate | AAF22695 | AF098239 |
| Streptavidin | S11540 | S11540 |

Therapeutic Moieties:

In some aspects thereof, the present invention employ conjugates of an antibody and a therapeutic moiety. To this end, in one example, first and second polynucleotides encoding the antibody and the therapeutic moiety, respectively, are ligated in frame, so as to encode an immunotoxin. The following table provide examples of sequences of therapeutic moieties.

| Therapeutic Moiety | Amino Acid sequence (Genebank Accession No.) | Nucleic Acid sequence (Genebank Accession No.) |
|---|---|---|
| *Pseudomonas* exotoxin | AAB25018 | S53109 |
| *Diphtheria* toxin | E00489 | E00489 |
| interleukin 2 | CAA00227 | A02159 |
| CD3 | P07766 | X03884 |
| CD16 | AAK54251 | AF372455 |
| interleukin 4 | P20096 | ICRT4 |
| HLA-A2 | P01892 | K02883 |
| interleukin 10 | P22301 | M57627 |
| Ricin A toxin | 225988 | A23903 |

Chemical Conjugates:

Many methods are known in the art to conjugate or fuse (couple) molecules of different types, including peptides. These methods can be used according to the present invention to couple an antibody another moiety, such as a therapeutic moiety or an identifiable moiety, to thereby provide an immunotoxin or immunolabel.

Two isolated peptides can be conjugated or fused using any conjugation method known to one skilled in the art. A peptide can be conjugated to an antibody of interest, using a 3-(2-pyridyldithio)propionic acid N-hydroxysuccinimide ester (also called N-succinimidyl 3-(2pyridyldithio) propionate) ("SDPD") (Sigma, Cat. No. P-3415), a glutaraldehyde conjugation procedure or a carbodiimide conjugation procedure.

SPDP Conjugation:

Any SPDP conjugation method known to those skilled in the art can be used. For example, in one illustrative embodiment, a modification of the method of Cumber et al. (1985, Methods of Enzymology 112: 207–224) as described below, is used.

A peptide, such as an identifiable or therapeutic moiety, (1.7 mg/ml) is mixed with a 10-fold excess of SPDP (50 mM in ethanol) and the antibody is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS.

The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation:

Conjugation of a peptide (e.g., an identifiable or therapeutic moiety) with an antibody can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques", Academic Press, San Diego) described below, is used.

The antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide Conjugation:

Conjugation of a peptide with an antibody can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and an hydroxyl, amino or sulfhydryl group of the peptide. See, generally, J. March, Advanced Organic Chemistry: Reaction's, Mechanism, and Structure, pp. 349–50 & 372–74 (3d ed.), 1985. By means of illustration, and not limitation, the peptide is conjugated to an antibody via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989);

Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Production of Biotinylated scMHC/Peptide Complexes:

Single-chain MHC/peptide complexes were produced by in vitro refolding of inclusion bodies produced in E. coli, as described previously (23, 24, U.S. patent application Ser. No. 09/534,966 and PCT/IL01/00260 (published as WO 01/72768). Biotinylation was performed using the BirA enzyme (Avidity, Denver, Colo.) as previously described (25).

Mice Immunization:

$D^{b-}/^-$ X β32 microglobulin (µ2m) null mice, transgenic for a recombinant HLA-A2.1/$D^b$-β2 microglobulin single chain (HHD mice) (26) were immunized with an emulsion containing purified protein-derived peptide of tuberculin (PPD) covalently coupled with HLA-A2/G9-209 complexes, as described previously (17). Briefly, mice were initially immunized subdermally and subsequently subcutaneously for two-week intervals for a period of 3–5 months with 20–30 µg/mice of the antigenic mixture in incomplete Freund's adjuvant. Spleens were collected two weeks after the last immunization.

Library Construction and Selection of Phage-Antibodies on Biotinylated Complexes:

Total RNA was isolated from immunized mice and an antibody scFv library was constructed by room temperature-PCR from the mRNA as described (27). The scFv repertoire was cloned as an SfiI-NotI fragment into the pCANTAB5E or pCC-CBD phagemid vectors (28). The complexity of both libraries was $1 \times 10^8$ independent clones. For panning, biotinylated scHLA-A2/G9-209M complexes (20 µg) were incubated with streptavidin-coated magnetic beads ($2 \times 10^8$), washed, and incubated with $10^{11}$ cfu of the libraries (1 hour at room temperature). Starting with the $2^{nd}$ round, panning was performed in the presence of an excess (5 µg) of scHLA-A2/G9-280V complexes. Beads were washed extensively 10–12 times with 2% MPBS+0.1% TWEEN20. Bound phages were eluted by using 1 ml of Triethylamine (100 mM, pH 12) for 5 minutes at room temperature followed by neutralization with 0.1 ml of 1 M Tris-HCl, pH 7.4. Eluted phages were expanded in exponentially growing E. coli TG1 cells that were later superinfected with M13KO7 helper phage as described (28).

Expression and Purification of Soluble Recombinant scFv and scFv-P38 Fusion Protein:

The G1 scFv gene was rescued from the phage clone by PCR and was subcloned into the phagemid vector pCANTAB6 by using the SfiI-NotI cloning sites. A Myc and hexahistidine tags were fused to the C-terminus of the scFv gene. The scFv antibody was expressed in BL21 λDE3 cells as previously described (29) and purified from the periplasmic fraction by metal-ion affinity chromatography. For the expression of the G1scFv-PE38 fusion protein, the scFv gene was subcloned as an NcoI-NotI fragment into the plasmid pIB-NN, which encodes the translocation and ADP-ribosylation domains of PE (PE38). Expression in BL21 λDE3 cells, refolding from inclusion bodies, and purification of G1scFv-PE38 was performed as previously described (30).

ELISA with Phage Clones and Purified scFv or scFv-PE38:

Binding specificity studies were performed by ELISA using biotinylated scMHC-peptide complexes. Briefly, ELISA plates (Falcon) were coated overnight with BSA-biotin (1 µg/well), washed, incubated (1 hour, room temperature) with streptavidin (1 µg/well), again washed extensively and further incubated (1 hour, room temperature) with 0.5 µg of MHC/peptide complexes. Plates were blocked with PBS/2% milk (30 minutes, room temperature), incubated with phage clones (about $10^9$ phages/well, 1 hour, room temperature) or 0.5–1 µg of soluble scFv or scFv-PE38, and afterwards washed with 1:1000 HRP-conjugated/anti-M 13, anti-myc antibody or anti-PE antibody, respectively. The HLA-A2-restricted peptides used for specificity studies are gp100 (154): KTWGQYWQV (SEQ ID NO:1); gp100 (209): IMDQVPFSV (SEQ ID NO:2); gp100 (280): YLEPGPVTV (SEQ ID NO:3); MUC1: LLLTVLTVL (SEQ ID NO:4); HTLV-1 (TAX): LLFGYPVYV (SEQ ID NO:5); hTEroom temperature (540): ILAKFLHWL (SEQ ID NO:6); hTEroom temperature (865): RLVDDFLLV (SEQ ID NO:7).

Flow Cytometry:

The B cell line RMAS-HHD transfected with a single-chain β2M-HLA-A2 gene (26) or the EBV-transformed B-lymphoblast JY cells ($10^6$ cells) were washed twice with serum-free RPMI and incubated overnight at 26° C. or 37° C., respectively, in medium containing 100 µM of the peptide. The APCs were subsequently incubated at 37° C. for 2–3 hours to stabilize cell surface expression of MHC-peptide complexes, followed by incubation with recombinant scFv (10–50 µg/ml, 60–90 minutes, 4° C.) in 100 µl. The cells were then washed, incubated with FITC-labeled anti-Myc antibody (30–45 minutes, 4° C.), and finally washed and analyzed by a FACStar flow cytometer (Becton Dickinson).

Competition Binding Assays:

Flexible ELISA plates were coated with BSA-biotin and scMHC-peptide complexes (10 μg in 100 μl) were immobilized thereto. The recombinant G1scFv-PE38 was labeled with [$^{125}$I] using the Bolton-Hunter reagent. Labeled protein was added to wells as a tracer (3–5×10$^5$ CPM/well) in the presence of increasing concentrations of the cold G1scFv-PE38 as a competitor and incubated at room temperature for 1 hour in PBS. The plates were washed thoroughly with PBS and the bound radioactivity was determined by a gamma counter. The apparent affinity of the G 1 scFv-PE38 was determined by extrapolating the concentration of a competitor necessary to achieve 5 0% inhibition of [$^{125}$I]-labeled G1scFv-PE38 binding to the immobilized scMHC-peptide complex. Non-specific binding was determined by adding a 20–40-fold excess of unlabeled Fab.

Cytotoxicity Assays:

RMAS-HHD and JY APCs were loaded with the G9-209 peptide and control peptides as previously described. Peptide-loaded cells were subsequently incubated with increasing concentrations of G1scFv-PE38 and the inhibition of protein synthesis was determined by measuring the uptake of $^3$H-Leucine into cellular proteins, as previously described (30). IC$_{50}$ was determined as the concentration of G1scFv-PE38 required to inhibit protein synthesis by 50%. In competition assays, excesses of specific and non-specific HLA-A2-peptide complexes (35–50 μg/well) were added to wells 15 minutes before the addition of G1scFv-PE38.

Experimental Results

Generation of Recombinant Single-Chain MHC-Peptide Complexes with the Melanoma gp100-Derived Peptide G9-209M:

Gp100 is a melanocyte lineage-specific membrane glycoprotein consisting of 661 amino acids that is expressed in most melanoma cells (19–22). This protein is recognized by many HLA-A2-restricted, melanoma-reactive, tumor infiltrating-lymphocytes (TILs) that have been isolated from melanoma patients (19–22). Several T cell HLA-A2-restricted epitopes have been identified in gp100; they have been improved in MHC anchor positions for enhanced immunogenicity without altering T-cell specificity (31). The G9-209M (IMDQVPFSV, SEQ ID NO:2) peptide is one of three major immunogenic epitopes (19–22). Recombinant MHC-peptide complexes that present the G9-209M peptide were generated by using a single-chain MHC (scMHC) construct expressed in E. coli that has been described previously (23, 24, U.S. patent application Ser. No. 09/534,966 and PCT/IL01/00260 (published as WO 01/72768). The scMHC-peptide complexes are produced by in vitro refolding of inclusion bodies in the presence of the G9-209M or other HLA-A2-restricted peptides, followed by a purification protocol employing ion-exchange chromatography. The refolded gp100-derived and control scHLA-A2-peptide complexes were very pure, homogenous, and monomeric, as determined by analysis on SDS-PAGE and gel filtration chromatography. The G9-209M-containing scHLA-A2 complexes have been previously shown to be functional, by their ability to stimulate specific CTL lines and clones and stain G9-209M-specific T cells in the form of tetramers (23, 24).

Construction of an Antibody scFv Phage Library and Selection of a Phage that Binds HLA-A2/G9-209M Complexes with TCR-like Specificity:

For immunization purposes PPD was coupled to the purified complex and the D$^{b-}$/$^-$X β2 microglobulin (β2m) null mice transgenic for a recombinant HLA-A2.1/D$^b$-β2 microglobulin single chain (HHD mice) (26) was immunized therewith. These mice combine classical HLA transgenesis with selective destruction of murine class I H-2. Hence, unlike the classical HLA transgenics, these mice showed only HLA-A2.1-restricted responses with muli-epitope proteins such as intact viruses. Moreover, it is presume that these mice are a useful tool for immunization with HLA-A2-peptide complexes because they should be largely tolerant to HLA-A2 as a B-cell immunogen and thus may favor the generation of an antibody response directed against the MHC-restricted epitope when in complex with HLA-A2 (the specific tumor-associated peptide). PPD was used for conjugation because it is a highly reactive T cell immunogen (17).

Total spleen mRNA was isolated from immunized mice and reverse transcribed to cDNA. Specific sets of degenerated primers were used to PCR-amplify the cDNA segments corresponding to the immunoglobulin heavy and light chain variable domains (27). The VH and VL PCR pools were assembled into a scFv repertoire by a PCR overlap extension reaction and subsequently cloned into the pCANTAB5E phagemid vector or to the phagemid vector pCC-Gal6(Fv) in which the scFv is expressed as an in frame fusion protein with a cellulose-binding domain (CBD) (28). The resulting libraries were transduced into E. coli TG1 cells by electroporation and expressed as fusion with the minor phage coat protein pIII after rescue with a helper phage. The library complexity consisted of 1×10$^8$ independent clones using both types of vectors.

The library was subjected to 3–4 panning cycles followed by elution of bound phages and reamplification in E. coli. To enhance the efficiency of selection biotinylated scMHC-peptide complexes were used. A BirA sequence tag for site-specific biotinylation was engineered at the C-terminus of the HLA-A2 gene as previously described (25). Several selection strategies were employed, the most successful of which resulted in the isolation of specific binders consisting of panning protocols with a negative depletion step starting from the 2$^{nd}$ round of panning. The specific HLA-A2/G9-209M biotinylated complexes were immobilized onto streptavidin-coated magnetic beads and the library was incubated with the immobilized complex in the presence of a large excess of HLA-2 complexes that displayed a different gp100-derived epitope, the G9-280V peptide. When this strategy is used G9-209M-specific phage will bind to streptavidin-biotin-immobilized complexes that are captured by a magnetic force, whereas pan-MHC binders that are not specific to the G9-209M peptide in the complex will bind to the non-specific complex in the solution and thus can be separated and removed from the specific phage. As shown in Table 1 below, a progressive, marked enrichment for phages that bind the immobilized complexes was observed after 3–4 rounds of panning, two of which were performed with the negative depletion strategy.

TABLE 1

Phage selection on scHLA-A2/G9-209M complexes

| Library | Cycle | Input | Output | Enrichment |
|---|---|---|---|---|
| scFv | 1 | 1 × 10$^{12}$ | 1 × 10$^4$ | — |
|  | 2 | 5 × 10$^{11}$ | 1 × 10$^5$ | 10 |
|  | 3 | 5 × 10$^{11}$ | 1 × 10$^9$ | 10,000 |

TABLE 1-continued

Phage selection on scHLA-A2/G9-209M complexes

| Library | Cycle | Input | Output | Enrichment |
| --- | --- | --- | --- | --- |
| scFv-CBD | 1 | $5 \times 10^9$ | $1 \times 10^4$ | — |
|  | 2 | $5 \times 10^{11}$ | $1 \times 10^5$ | 10 |
|  | 3 | $5 \times 10^{11}$ | $1 \times 10^8$ | 1,000 |

A $4^{th}$ round of selection resulted with similar enrichments as observed in round 3.

Figure 1B:
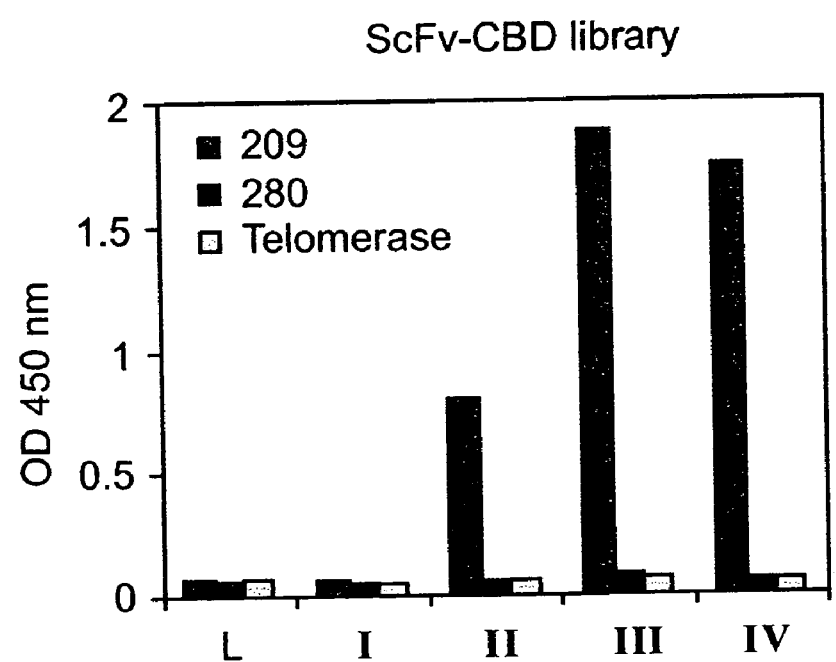

Polyclonal phage ELISA was performed to determine phage specificity on biotinylated recombinant scMHC-peptide complexes immobilized to BSA-Biotin-streptavidin-coated immunoplates. The BSA-biotin-streptavidin spacer enables the correct presentation of the complexes, which can be distorted by direct binding to plastic. Phage analyzed already after the $2^{nd}$ and more dramatically, after the $3^{rd}$ round of panning revealed a unique specificity pattern only directed toward the specific G9-209M-containing HLA-A2 complexes (FIGS. 1A–B). No binding was observed with control HLA-A2 complexes that display the gp100-derived epitope, G9-280V or the telomerase-derived epitope 654.

Figure 2A:
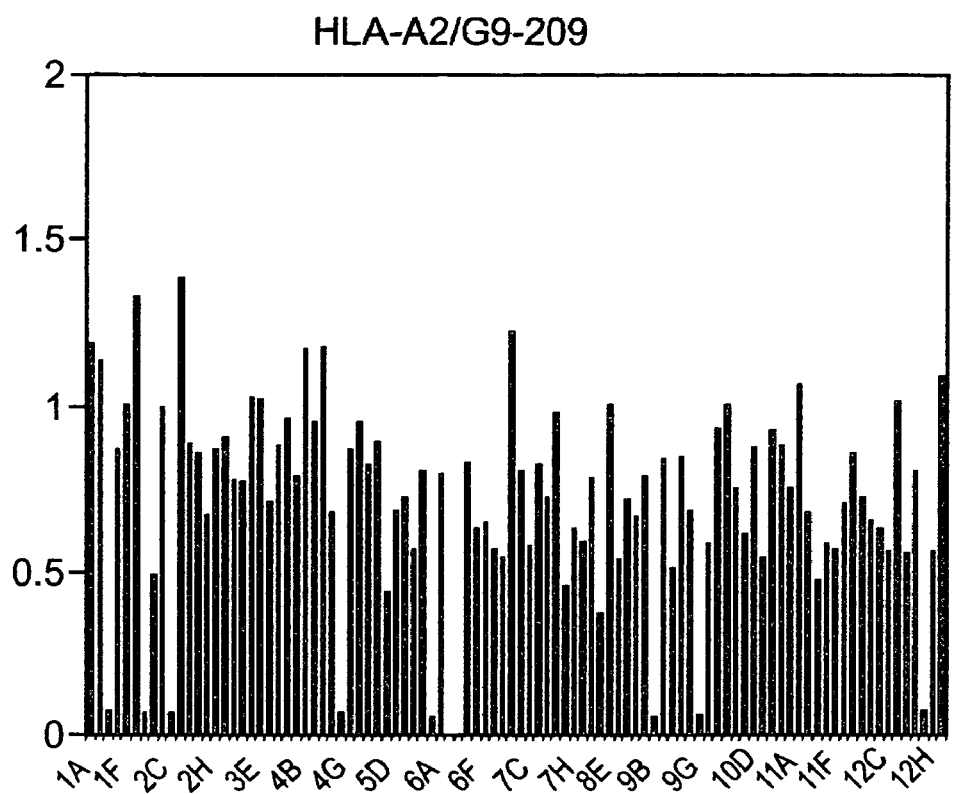
Figure 2B:
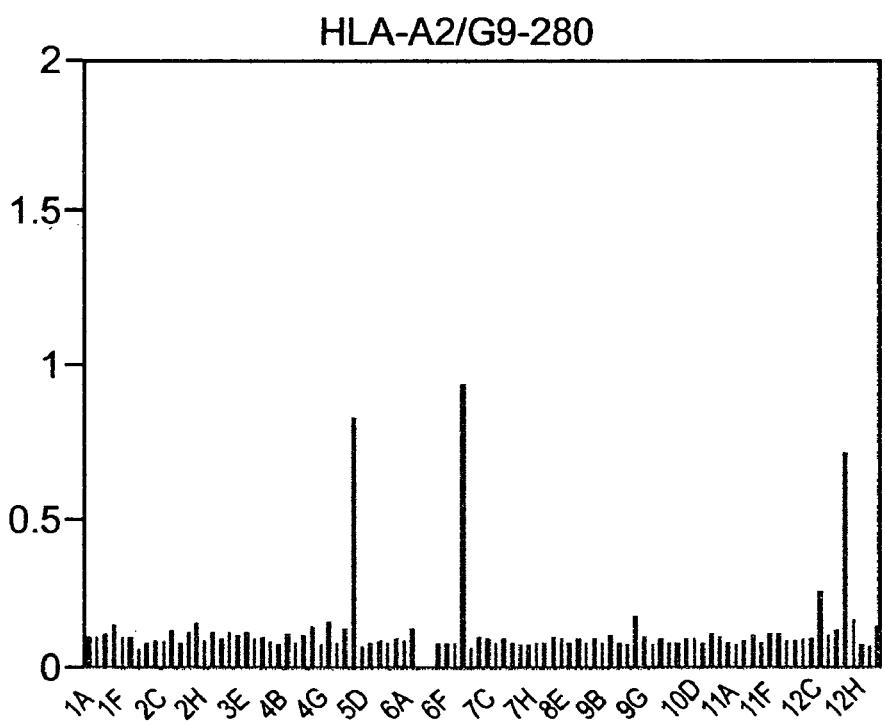

Individual monoclonal phage clones were isolated from the population of phages from the last round of panning (no further enrichment observed after a 4th round) and re-screened for specificity by phage ELISA (FIGS. 2A–B). Of the 93 clones tested, 85 (91%) reacted with the HLA-A2/G9-209M complex (FIG. 2A). Seventy-seven out of the 85 reactive clones (90%) reacted specifically with the specific HLA-A2/G9-209M complex but not with the control G9-280V-containing complex (FIG. 2B). Only a small percentage of the clones (5/93; 5%) did not exhibit peptide specificity (FIG. 2B). Thus, the panning procedure yielded a successful enrichment of phage antibodies with TCR-like specificity toward the HLA-A2/G9-209M complex. Fingerprint analysis by means of multicutter restriction enzyme digestion revealed that 50 positive, HLA-A2/G9-209M-specific clones had a similar digestion pattern, indicating that all are similar (data not shown). Similar results were obtained with the two libraries. Since they were constructed from the same genetic material (the same pool of mRNA), only phage clones derived from the pCANTAB5E scFv library were further characterized.

DNA sequencing of VH and VL variable domains from 10 clones revealed that all were identical (data not shown), suggesting that they were all derived from a single productive antibody VH/VL combinatorial event.

Figures 3A, 3B, 3C:
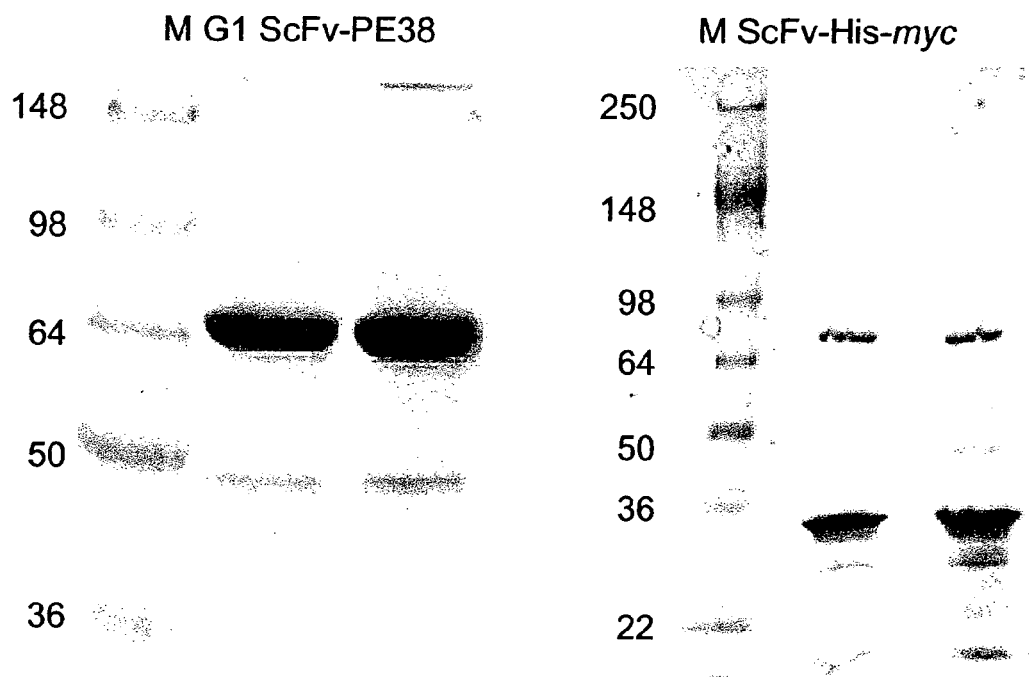

Characterization of the Soluble Recombinant scFv Antibody with TCR-Like Specificity:

DNA sequencing revealed that the antibody VH sequence belongs to the mouse heavy chains subgroup III (D) and the VL sequence to mouse kappa light chains group IV (according to Kabbat). The nucleotide sequence (SEQ ID NO:8) and deduced amino acid sequence (SEQ ID NO:9) are shown in FIG. 3A. To further characterize the binding specificity and the biological properties of the selected scFv antibody, termed G1, two expression systems were used; for the first, the scFv was subcloned into the phagemid vector pCANTAB6 in which a myc and a hexahistidine tag is fused to the C-terminus of the scFv gene. The second was a T7 promoter-driven expression system in which the scFv gene is fused to a truncated form of Pseudomonas Exotoxin A (PE38) to generate a scFv-immunotoxin (12). This truncated form of PE contains the translocation and ADP-ribosylation domains of whole PE but lacks the cell-binding domain, which is replaced by the scFv fragment fused at the N-terminus of the truncated toxin. The G1 scFv was produced in E. coli BL21 (λDE3) cells by secretion and was purified from periplasmic fractions by metal affinity chromatography using the hexahistidine tag fused to the C-terminus (FIG. 3B). The G1 scFv-PE38 was expressed in BL21 cells and upon induction with IPTG, large amounts of recombinant protein accumulated as intracellular inclusion bodies. SDS-PAGE showed that inclusion bodies from cultures expressing G1 scFv-PE38 contained more than 90% recombinant protein. Using established renaturation protocols, G1 scFv-PE38 was refolded from solubilized inclusion bodies in a redox-shuffling refolding buffer and was thereafter purified by ion-exchange chromatography on Q-Sepharose and MonoQ columns, and later by size-exclusion chromatography. A highly purified G1 scFv-PE38 fusion protein with the expected size of 63 kDa was obtained as analyzed by SDS-PAGE under non reducing conditions (FIG. 3C). The molecular profile of the G1scFv and G1scFv-immunotoxin was analyzed by size-exclusion chromatography and revealed a single protein peak in a monomeric form with an expected molecular mass of 26 and 63 kDa, respectively (data not shown). The yield of the refolded G1 scFv-immunotoxin was about 2%, thus, 2 mg of highly pure protein could be routinely obtained from the refolding of 100 mg of protein derived from inclusion bodies containing 80–90% of recombinant protein. This yield is similar to previously reported scFv-immunotoxins that expressed well and were produced using a similar expression and refolding system (30). The yield of the G1scFv was 3 mg from a 1-liter bacterial culture.

Figure 4:
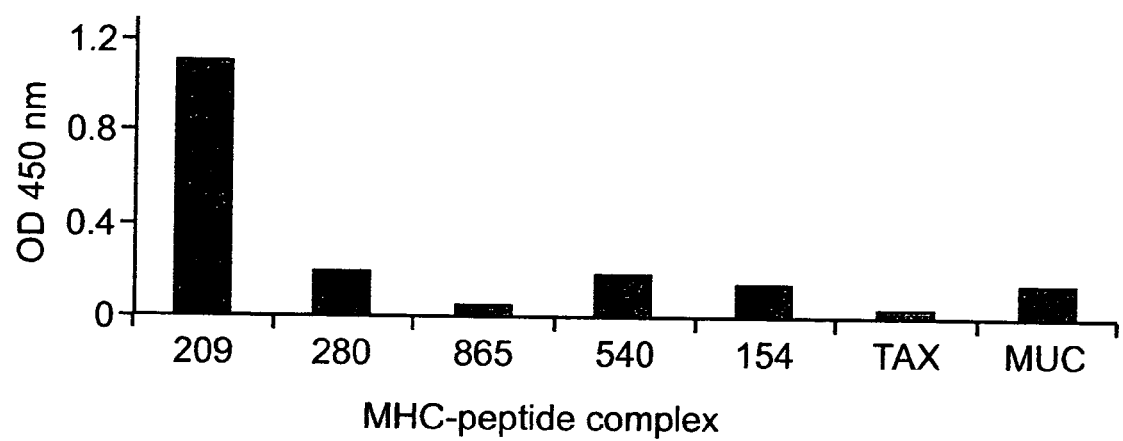

The binding specificity of the soluble purified G1 scFv antibody and G1 scFv-PE38 fusion protein was determined by ELISA assays on biotinylated MHC-peptide complexes immobilized to wells through BSA-biotin-streptavidin to ensure correct folding of the complexes, which can be distorted by direct binding to plastic. The correct folding of the bound complexes and their stability during the binding assays were determined by their ability to react with the conformational, specific monoclonal antibody w6/32, which binds HLA complexes only when folded correctly and when it contains peptide (data not shown). When we used the soluble-purified G1 scFv or G1scFv-PE38 protein, the ELISA assays revealed a very specific recognition pattern corresponding to the hallmarks of MHC-restricted T-cell specificity (FIG. 4). The G1 scFv selected to bind the G9-209M-containing HLA-A2 complex reacted only with the specific complex and not with complexes displaying the G9-280 and G9-154 gp100-derived MHC-peptide complexes nor to other control complexes containing HLA-A2-restricted telomerase-derived epitopes 540 and 865 (32), a MUC1-derived peptide (33), or the HTLV-1-derived TAX peptide (34) (FIG. 4). In these assays the binding was detected with an anti-PE38 antibody. Similar results were obtained when using the unfused G1 scFv antibody where detection was performed with anti-Myc tag antibody (data not shown). Thus, this antigen-specific scFv fragment exhibits binding characteristics and the fine specificity of a TCR-like molecule. The G1 scFv or G1 scFv-PE38 did not recognize the peptide alone nor empty HLA-A2 molecules (which are difficult to produce because they are unstable in the absence of a peptide), neither streptavidin nor other protein antigens (data not shown).

Figure 5A:
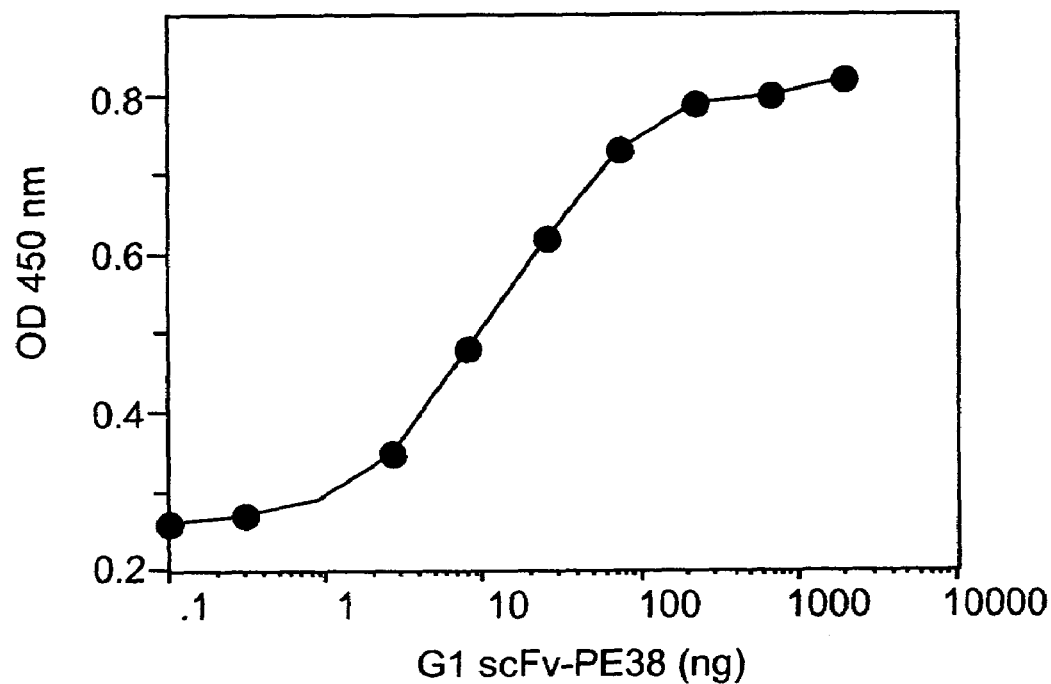
Figure 5B:
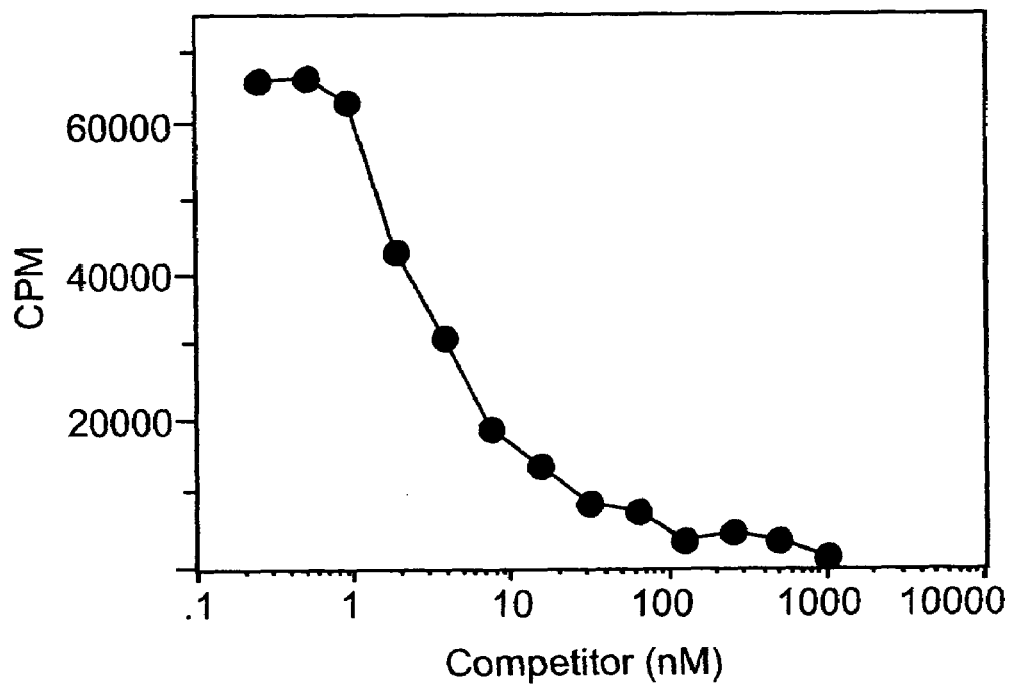

Next, the binding properties of the TCR-like soluble purified G1 scFv-PE38 were determined using a saturation ELISA assay in which biotinylated complexes were bound to BSA-biotin-streptavidine-coated plates to which increasing amounts of G1 scFv-PE38 were added. The binding of G1scFv-PE38 to the specific gp100-derived HLA-A2/G9-209M complex was dose-dependent and saturable (FIG. 5A). Extrapolating the 50% binding signal revealed that this antibody possessed high affinity, with a binding affinity in the nanomolar range. To determine the apparent binding affinity of the TCR-like scFv fragments to its cognate MHC-peptide complex, a competition binding assay was performed in which the binding of $^{125}$I-labeled G1scFv-PE38 was competed with increasing concentrations of unlabeled protein. These binding assays revealed an apparent binding affinity in the low nanomolar range of 5 nM (FIG. 5B). Importantly, these results underscore a previous success in isolating a high affinity scFv antibody with TCR-like specificity from the phage-displayed antibody repertoire of immunized HLA-A2 transgenic mice.

Binding of G1 scFv to APCs Displaying the gp100-Derived Epitope:

To demonstrate that the isolated soluble G 1 scFv can bind the specific MHC-peptide complex, not only in its recombinant soluble form but also in the native form, as expressed on the cell surface, two APC systems were utilized. One consisted of the murine TAP2-deficient RMA-S cells that were transfected with the human HLA-A2 gene in a single-chain format (26) (HLA-A2.1/Db-β2m single chain) (RMA-S-HHD cells). The gp100-derived peptide and control peptides were loaded on the RMA-S—HHD cells and the ability of the selected G1 scFv antibody to bind to peptide-loaded cells was monitored by FACS (FIGS. 6A–C). Peptide-induced MHC stabilization of the TAP2 mutant RMA-S-HHD cells was determined by analyzing the reactivity of the conformational anti HLA antibody w6/32 and the anti-HLA-A2 MAb BB7.2 with peptide loaded and unloaded cells (FIGS. 6A and B). The G1 scFv, which recognized the G9-209M-containing HLA-A2 complex, reacted only with RMA-S-HHD cells loaded with the G9-209M peptide but not with cells loaded with the G9-280 peptide (FIG. 6C) or control cells not loaded with peptide. The G1 scFv did not bind to cells loaded with other HLA-A2-restricted control peptides such as TAX, MUC1 or telomerase-derived peptides used for the specificity analysis (see FIG. 4).

A second type of APCs was also used, namely the EBV-transformed B lymphoblast JY cells, which express HLA-A2; these cells were incubated with the gp100-derived or control peptides. They are TAP+, and consequently, the displaying of the exogenously supplied peptide is facilitated by peptide exchange. Using this strategy, a similar binding specificity with the G1 scFv antibody was observed (data not shown). These results demonstrate that the scFv antibody can specifically recognize its corresponding native HLA-A2 complex in situ on the surface of cells.

Cytotoxic Activity of G1scFv-PE38 Toward APCs:

To determine the ability of the G1 scFv antibody to serve as a targeting moiety for T cell-like specific elimination of antigen-presenting cells, a G1scFv-PE38 molecule was constructed in which the very potent truncated form of *Pseudomonas* exotoxin A is fused to the C-terminus of the scFv gene and its ability to kill peptide-loaded APCs was tested. RMAS-HHD or JY cells were loaded with the gp100-derived epitopes G9-209M and G9-280V as well as with other control HLA-A2-restricted peptides. FACS analysis with anti-HLA-A2 antibody revealed a similar expression pattern of HLA-A2 molecules with G9-209M, G9-280V, and other control peptide-loaded cells (FIG. 6B). As shown in FIG. 7A, cytotoxicity by G1scFv-PE38 was observed only on RMAS-HHD cells loaded with the G9-209 peptide with an $IC_{50}$ of 10–20 ng/ml. No cytotoxic activity was observed on RMAS-HHD cells that were loaded with the gp100-derived G9-280V epitope or with other control HLA-A2-restricted peptides or cells that were not loaded with peptide. G9-209M-loaded RMAS-HHD cells were not killed with an irrelevant immunotoxin in which an anti human Lewis Y scFv antibody is fused to PE38 [B3(Fv)-PE38] (FIG. 7A). In the EBV-transformed JY cells, which express normal TAP, the display of the exogenously-supplied peptide is facilitated by peptide exchange. Using this strategy, similar specific activity was observed in which G1scFv-PE38 kills only cells loaded with the G9-209M peptide (FIG. 7B). Additional proof for specificity was demonstrated in competition experiments in which excess specific and control soluble scHLA-A2-peptide complex was present in solution, in order to compete for binding and inhibit cytotoxicity by G1 scFv-PE38. An example of this type of assay is shown in FIG. 7C, in which excess soluble G9-209M-containing HLA-A2 but not the G9-280V/HLA-A2 complex competed and inhibited the cytotoxic activity of G1 scFv-PE38 toward G9-209M-loaded JY cells. These results further demonstrate the fine and unique specificity of the G1scFv antibody and its ability to serve as a targeting moiety to deliver a cytotoxic effector molecule with antigen (peptide)-specific, MHC-restricted specificity of T cells directed toward a human tumor T-cell epitope.

Discussion of the Results

In this example, the ability to select from an immune repertoire of murine scFv fragments a high affinity antibody (referred to herein as G1scFv) directed toward a human T-cell epitope derived from a cancer antigen, the melanoma-associated antigen gp100, was demonstrated.

G1scFv exhibits a very specific and special binding pattern; it can bind in a peptide-specific manner to HLA-A2 complexes. Hence, this is a recombinant antibody with T-cell antigen receptor-like specificity. In contrast to the inherent low affinity of TCRs, this molecule displays the high affinity binding characteristics of antibodies, while retaining TCR specificity.

This example strikingly demonstrates the power of the phage display approach and its ability to select especially fine specificities from a large repertoire of different antibodies.

The ability to select high-affinity TCR-like antibodies, despite the fact that such peptide-specific binders are thought to be rare and hence difficult to isolate, may result from the following considerations.

One is the mode of immunization and selection which included immunization of transgenic animal combined with the power of various selection strategies employed by phage display. It is believed that using HLA transgenic mice, such as HLA-A2 transgenic mice, is an advantage because they are usually tolerant to HLA complexes unless a new foreign peptide is presented on the complex. The ability to isolate TCR-like antibody molecules may represent a situation in which lymphocytes that were tolerant to HLA-A2 are now exposed to new epitopes contributed, in the example provided herein, by the melanoma gp100-derived peptide presented on HLA-A2. The panning procedure that combined an excess of non-specific complex in solution significantly contributed to the selection process and allowed to isolate a rare antibody clone (one out of $10^8$).

Another important issue relates to the state of the antigen used in the selection process. The conformation of the antigen has to be as "natural" as possible, especially when produced in a recombinant form. As described in references 23 and 24 and in U.S. patent application Ser. No. 09/534,966 and PCT/IL01/00260 (published as WO 01/72768), it was found that in vitro refolding from inclusion bodies produced in E. coli of a single-chain MHC molecule complexed with various peptides yields large amounts of correctly folded and functional protein. The fact that the exemplary antibody G1scFv was isolated from a relatively small library of about $10^8$ clones, yet is highly specific with an affinity in the nanomolar range, strongly indicates that the HLA-A2 transgenic mice that was used for immunization indeed developed high-affinity antibodies to the HLA-A2/G9-209 complexes. The observation that only a single anti-HLA-A2/G9-209 antibody was isolated may reflect that only one such specificity exists or that other specificities were not generated during the immune response because such a response could not be easily generated and tolerated by the HLA-A2 transgenic mice. Quite astonishing is the fact that similar results were reported in the past for a murine MHC-peptide system where, using phage display, a recombinant TCR-like antibody directed toward a class I murine $H-2K^k$ molecule in complex with the influenza hemagglutinin peptide $Ha_{255-262}$ was isolated (17). Similar to the results presented here, of the 50 clones tested, seven reacted specifically with the $H-2K^k/Ha_{255-262}$ complexes only, and not with other $H-2K^k$/peptide complexes. Interestingly, the DNA sequences of these specific clones were determined and found to be identical (17). These anti-$H-2K^k/Ha_{255-262}$ complexes antibodies, however, cannot be used to monitor antigen presentation and or kill antigen presenting cells of human origin.

Despite the fact that antibodies having a T-cell antigen receptor-like specificity are rare, the phage display approach can be applied to isolate recombinant antibodies with TCR-like specificity to a variety of MHC-peptide complexes related to various pathological conditions such as cancer, viral infections, and autoimmune diseases.

Recombinant antibodies with TCR-like specificity represent a new, valuable tool for future research in two major areas of tumor immunology. First, these antibodies may now be used to detect and directly visualize the presence of specific T-cell epitopes or MHC-peptide complexes by standard methods of flow cytometry and immuno-histochemistry. They should be very useful for the study and analysis of antigen presentation in cancer by determining the expression of specific tumor-related MHC-peptide complexes on the surface of tumor cells, metastasis, antigen-presenting cells, and lymphoid cells. Moreover, such antibodies can be used to analyze immunotheraphy-based approaches by determining the alterations in MHC-peptide complex expression on antigen-presenting cells before, during, and after vaccination protocols with peptides or with APCs loaded with tumor cell extracts or dendritic-tumor cell hybrid vaccinations (7–11). Thus, questions relating to how and where certain events occur during antigen presentation may be directly addressed, for the first time, and the expression of T-cell epitopes on the antigen-presenting cell may be visualized and quantitated.

Second, antibodies with such exquisitely fine specificity directed toward a very specific and unique human tumor antigen present new opportunities for use as targeting moieties for various antibody-based immunotherapeutic approaches. This includes using such antibodies to construct recombinant immunotoxins (12), fusion with cytokine molecules (37) or for bi-specific antibody therapy (38). The open question with respect to these applications relates to the low density of the specific epitope on the target cell's surface. It has been previously demonstrated, using the murine $H-2K^k$/influenza hemagglutinin peptide complex and a similar antigen-presenting system that to achieve efficient killing with a TCR-like immunotoxin molecule, a density of several thousand particular MHC-peptide complexes are required for the selective elimination of APCs (39). The results of described herein support these findings, achieving a similar cytotoxic potential of a T-cell-like immunotoxin. To improve the targeting capabilities of these TCR-like antibody molecules, two antibody engineering approaches can be employed: (i) to increase the affinity of the parental antibody by affinity maturation strategies without altering its TCR-like fine specificity (40); and (ii) to increase the avidity of these recombinant monovalent molecules by making them bi-valent (38). Combining these strategies will result in second generation, improved molecules that will be valuable tools for immunotherapeutic approaches as well as serve as innovative research tools for studying the interaction of tumor cells and the human immune system.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by a Genebank accession number mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES

Additional References are Cited in the Text

1. Boon, T., & van der Bruggen, P. (1996) *J Exp Med* 183,725–9.
2. Rosenberg, S. A. (2001) *Nature* 411,380-(4.
3. Renkvist, N., Castelli, C., Robbins, PF, & Parmiani, G. (2001) *Cancer Immunol Immunother* 50, 3–15.
4. Anichini A, Maccalli C, Mortarini R, Salvi S, Mazzocchi A, Squarcina P, Herlyn M, Parmiani G. (1993) *J. Exp. Med.* 177, 989–998.
5. Coulie P G, Brichard V, Van Pel A, Wolfel T, Schneider J, Traversari C, Mattei S, De Plaen E, Lurquin C, Szikora J P, et al. (1994) *J. Exp. Med.* 180, 35–42.
6. Rivoltini L, Loftus D J, Squarcina P, Castelli C, Rini F, Arienti F, Belli F, Marincola F M, Geisler C, Borsatti A, Appella E, Parmiani G. (1998) *Crit Rev Immunol* 18,55–63.
7. Offringa, R., van der Burg, S. H., Ossendorp, F. Toes, R. E., & Melief, C. J. (2000) *Curr Opin Immunol* 12, 576–82
8. Restifo N P, Esquivel F, Kawakami Y, Yewdell J W, Mule J J, Rosenberg S A, Bennink J R. (1993) *J. Exp. Med.* 177,265–272.

9. Seliger, B., Maeurer, M. J., & Ferrone, S (2000) *Immunol. Today* 21, 455–464.
10. Esche, C., Shurin, M. R., Lotze, M. T., (1999) *Curr Opin Mol Ther* 1,72–81.
11. Kugler A, Stuhler G, Walden P, Zoller G, Zobywalski A, Brossart P, Trefzer U, Ullrich S, Muller C A, Becker V, Gross A J, Hemmerlein B, Kanz L, Muller G A, Ringert R H. *Nat. Med.* 6, 332–336 (2000).
12. Pastan, I. (1997) *Biochim Biophys Acta.* 1333,C1–6.
13. Porgador, A., Yewdell, J. W., Deng, Y., Bennink, J. R., Germain, R. N., (1997) *Immunity* 6, 715–26
14. Dadaglio, G, Nelson, C A, Deck, M B, Petzold, S J, Unanue, E R. (1997) *Immunity* 6,727–38.
15. Aharoni, R, Teitelbaum, D, Arnon, R, Puri, J. (1991) *Nature.*351,147–50.
16. Krogsgaard M, Wucherpfennig K W, Canella B, Hansen B E, Svejgaard A, Pyrdol J, Ditzel H, Raine C, Engberg J, Fugger L. (2000) *J Exp Med.* 191,1395–412.
17. Andersen P S, Stryhn A, Hansen B E, Fugger L, Engberg J, Buus S. (1996) *Proc. Natl. Acad. Sci. U.S. A* 93, 1820–1824.
18. Chames, P., Hufton, S. E., Coulie, P. G., Uchanska-Ziegler, B. & Hoogenboom, H. R. (2000) *Proc. Natl. Acad. Sci. U.S. A* 97, 7969–7974.
19. Kawakami Y, Eliyahu S, Delgado C H, Robbins P F, Sakaguchi K, Appella E, Yannelli J R, Adema G J, Miki T, Rosenberg S A. (1994) *Proc. Natl. Acad. Sci. U. S. A* 91, 6458–6462.
20. Bakker A B, Schreurs M W, de Boer A J, Kawakami Y, Rosenberg S A, Adema G J, Figdor C G. (1994) *J. Exp. Med.* 179, 1005–1009.
21. Kawakami Y, Eliyahu S, Jennings C, Sakaguchi K, Kang X, Southwood S, Robbins P F, Sette A, Appella E, Rosenberg S A. (1995) *J. Immunol.* 154, 3961–3968.
22. Cox A L, Skipper J, Chen Y, Henderson R A, Darrow T L, Shabanowitz J, Engelhard V H, Hunt D F, Slingluff C L Jr. (1994) *Science* 264, 716–719.
23. Denkberg, G., Cohen, C. J., Segal, D., Kirkin, A. F. & Reiter, Y. (2000) *Eur. J Immunol.* 30, 3522–3532.
24. Denkberg, G., Cohen, C. J., & Reiter, Y. (2001) *J Immunol* 167,270–6.
25. Altman J D, Moss P A, Goulder P J, Barouch D H, McHeyzer-Williams M G, Bell J I, McMichael A J, Davis M M. [published erratum appears in Science 1998 Jun. 19;280(5371):1821]. (1996) Science 274, 94–96.
26. Pascolo S, Bervas N, Ure J M, Smith A G, Lemonnier F A, Perarnau B. (1997) *J Exp Med.* 185,2043–51.
27. Benhar, I, and Reiter, Y. *Curr. Protocols in Immunology* in press (2001)
28. Berdichevsky Y, Ben-Zeev E, Lamed R, Benhar I. (1999) *J Immunol Methods.* 228:151–62.
29. de Haard H J, van Neer N, Reurs A, Hufton S E, Roovers R C, Henderikx P, de Bruine A P, Arends J W, Hoogenboom H R. (1999) *J Biol. Chem.* 274,18218–30.
30. Brinkmann U, Pai L H, FitzGerald D J, Willingham M, and Pastan I. (1991) *Proc Natl Acad Sci U S A.* 88:8616–20.
31. Parkhurst M R, Salgaller M L, Southwood S, Robbins P F, Sette A, Rosenberg S A, Kawakami Y. (1996) *J Immunol.* 157:2539–48.
32. Vonderheide, R. H., Hahn, W. C., Schultze, J. L. & Nadler, L. M. (1999) *Immunity.* 10, 673–679.
33. Carmon L, El-Shami K M, Paz A, Pascolo S, Tzehoval E, Tirosh B, Koren R, Feldman M, Fridkin M, Lemonnier F A, Eisenbach L. (2000) *Int J Cancer.*85,391–7.
34. Bieganowska K, Hollsberg P, Buckle G J, Lim D G, Greten T F, Schneck J, Altman J D, Jacobson S, Ledis S L, Hanchard B, Chin J, Morgan O, Roth P A, Hafler D A. (1999) *J Immunol.* 162, 1765–1771.
35. Lee P P, Yee C, Savage P A, Fong L, Brockstedt D, Weber J S, Johnson D, Swetter S, Thompson J, Greenberg P D, Roederer M, Davis M M. (1999) *Nat. Med.* 5, 677–685.
36. Ogg G S, Jin X, Bonhoeffer S, Dunbar P R, Nowak M A, Monard S, Segal J P, Cao Y, Rowland-Jones S L, Cerundolo V, Hurley A, Markowitz M, Ho D D, Nixon D F, McMichael A J. (1998) *Science* 279, 2103–2106.
37. Lode, H. N., & Reisfeld, R. A. (2000) *Immunol Res.* 21,279–88.
38. Withoff, S., Helfrich, W., de Leij, L F., Molema, G. (2001) *Curr Opin Mol Ther.* 3,:53–62.
39. Reiter, Y., Di Carlo, A., Fugger, L., Engberg, J. & Pastan, I. (1997) *Proc. Natl. Acad. Sci. U.S. A* 94, 4631–4636.
40. Chowdhury, P. S., & Pastan, I. (1999) *Nat Biotechnol.* 17, 568–72.
41. Garboczi, D. N., D. T. Hung, and D. C. Wiley. 1992. HLA-A2-peptide complexes: refolding and crystallization of molecules expressed in *Escherichia coli* and complexed with single antigenic peptides. Proc. Natl. Acad. Sci. USA 89:3429.
42. Mottez, E., P. Langlade-Demoyen, H. Gournier, F. Martinon, J. Maryanski, P. Kourilsky, and J. P. Abastado. 1995. Cells expressing a major histocompatibility complex class I molecule with a single covalently bound peptide are highly immunogenic. J. Exp. Med. 181:493.
43. Lone, Y.-C., Motta, I., Mottez, E., Guilloux, Y., Lim, A., Demay, F., Levraud, J., Kourilsky, P., and Abastado, J., 1998. In virto induction of specific cytotoxic T lymphocyes using recombinant single-chain class I/peptide complexes. *J Immunother.* 21:283.
44. Mage M G, Lee L, Ribaudo R K, Corr M, Kozlowski S, McHugh L, and Margulies D H 1992. A recombinant, soluble, single-chain class I major histocompatibility complex molecule with biological activity. *Proc Natl Acad Sci USA* 89:10658.
45. Lee L, McHugh L, Ribaudo R K, Kozlowski S, Margulies D H, and Mage M G. 1994. Functional cell surface expression by a recombinant single-chain class I major histocompatibility complex molecule with a cis-active beta 2-microglobulin domain. *Eur. J. Immunol.* 24: 2633.
46. Matsumura, M., Y. Saito, M. R. Jackson, E. S. Song, and P. A. Peterson. 1992. In vitro peptide binding to soluble empty class I major histocompatibility complex molecules isolated from transfected *Drosophila melanogaster* cells. J. Biol. Chem. 267:23589.
47. Stern, L. J., and D. C. Wiley. 1992. The human class II MHC protein HLA-DR1 assembles as empty heterodimers in the absence of antigenic peptide. Cell 68:465.
48. Altman, J. D., P. A. Reay, and M. M. Davis. 1993. Formation of functional Peptide complexes of class II major histocompatibility complex proteins from subunits produced in *Escherichia coli*. Proc. Natl. Acad. Sci. USA 90:10330.
49. Kozono, H., J. White, J. Clements, P. Marrack, and J. Kappler. 1994. Production of soluble MHC class II proteins with covalently bound single peptides. Nature 369: 151.

50. White, J., Crawford, F., Fremont, D., Marrack, P., and Kappler, J. 1999. Soluble class 1 MIC with b-2 microglobulin covalently linked peptides: specific binding to a T-cell hybridoma. *J. Immunol.* 162: 2671
51. Ignatowicz, L., G. Winslow, J. Bill, J. Kappler, and P. Marrack. 1995. Cell Surface expression of class II MHC proteins bound by a single peptide. J. Immunol.154:3852.
52. Ignatowicz, L., J. Kappler, and P. Marrack. 1996. The repertoire of T cells shaped by a single MHC/peptide ligand. Cell 84:521.
53. Uger, R. A., and B. H. Barber. 1998. Creating CTL targets with epitope-linked 2-microglobulin constructs. J. Immunol. 160:1598.
54. Cancer immunology immunotherapy 2001 50:3–15. A listing of human tumor antigens recognized by T cells.

What is claimed is:

1. An isolated protein comprising the amino acid sequence set forth in SEQ ID NO:9.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Artificial sequence
<220> FEATURE:
<223> OTHER INFORMATION: HLA-A2-restricted peptide, gp100 (154)

<400> SEQUENCE: 1

Lys Thr Trp Gly Gln Tyr Trp Gln Val
1               5

<210> SEQ ID NO 2
<211> LENGTH: 9
<212> TYPE: PRT
<213> ORGANISM: Artificial sequence
<220> FEATURE:
<223> OTHER INFORMATION: HLA-A2-restricted peptide, gp100 (209)

<400> SEQUENCE: 2

Ile Met Asp Gln Val Pro Phe Ser Val
1               5

<210> SEQ ID NO 3
<211> LENGTH: 9
<212> TYPE: PRT
<213> ORGANISM: Artificial sequence
<220> FEATURE:
<223> OTHER INFORMATION: HLA-A2-restricted peptide, gp100 (280)

<400> SEQUENCE: 3

Tyr Leu Glu Pro Gly Pro Val Thr Val
1               5

<210> SEQ ID NO 4
<211> LENGTH: 9
<212> TYPE: PRT
<213> ORGANISM: Artificial sequence
<220> FEATURE:
<223> OTHER INFORMATION: HLA-A2-restricted peptide, MUC1

<400> SEQUENCE: 4

Leu Leu Leu Thr Val Leu Thr Val Leu
1               5

<210> SEQ ID NO 5
<211> LENGTH: 9
<212> TYPE: PRT
<213> ORGANISM: Artificial sequence
<220> FEATURE:
<223> OTHER INFORMATION: HLA-A2-restricted peptide, HTLV-1 (TAX)

<400> SEQUENCE: 5

Leu Leu Phe Gly Tyr Pro Val Tyr Val
1               5

<210> SEQ ID NO 6
<211> LENGTH: 9
<212> TYPE: PRT
<213> ORGANISM: Artificial sequence
<220> FEATURE:
<223> OTHER INFORMATION: HLA-A2-restricted peptide, hTEroom temperature (540)

<400> SEQUENCE: 6

Ile Leu Ala Lys Phe Leu His Trp Leu
1               5

<210> SEQ ID NO 7
<211> LENGTH: 9
<212> TYPE: PRT
<213> ORGANISM: Artificial sequence
<220> FEATURE:
<223> OTHER INFORMATION: HLA-A2-restricted peptide, hTEroom temperature (865)

<400> SEQUENCE: 7

Arg Leu Val Asp Asp Phe Leu Leu Val
1               5

<210> SEQ ID NO 8
<211> LENGTH: 711
<212> TYPE: DNA
<213> ORGANISM: Artificial sequence
<220> FEATURE:
<223> OTHER INFORMATION: G1 Single chain Fv-recombinant antibody DNA sequence

<400> SEQUENCE: 8
caggtgaaac tgcaggagtc tgggggaggc ttagtgaagc ctggagggtc cctgaaactc      60
tcctgtgcag cctctggatt cactttcagt agctatggca tgtcttgggt tcgccagact     120
ccagacaaga ggctggagtg ggtcgcaacc attagtagtg gtggtagtta cacctactat     180
ccagacagtg tgaaggggcg attcaccatc tccagagaca tgccaagaa caccctgtac      240
ctgcaaatga gcagtctgaa gtctgaggac acagccatgt attactgtgc aagaggtaac     300
tgggaaggat ggtacttcga tgtctggggc caagggacca cggtcaccgt ctcctcaggt     360
ggaggcggtt caggcggagg tggctctggc ggtggcggat cgaacatcga gctcactcag     420
tctccagcaa tcatgtctgc atctccaggg gagagggtca ccatgacctg cagtgccagc     480
tcaagtatac gttacatata ttggtaccaa cagaagcctg gatcctcccc cagactcctg     540
atttatgaca catccaacgt ggctcctgga gtcccttttc gcttcagtgg cagtgggtct     600
gggacctctt attctctcac aatcaaccga atggaggctg aggatgctgc cacttattac     660
tgccaggagt ggagtggtta tccgtacacg ttcggagggg ggacaaagtt g              711

<210> SEQ ID NO 9
<211> LENGTH: 237
<212> TYPE: PRT
<213> ORGANISM: Artificial sequence
<220> FEATURE:
<223> OTHER INFORMATION: G1 single chain Fv- recombinant antibody protein sequence

<400> SEQUENCE: 9

Gln Val Lys Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr

-continued

```
                    20                  25                  30
Gly Met Ser Trp Val Arg Gln Thr Pro Asp Lys Arg Leu Glu Trp Val
            35                  40                  45
Ala Thr Ile Ser Ser Gly Gly Ser Tyr Thr Tyr Tyr Pro Asp Ser Val
 50                  55                  60
Lys Gly Arg Phe Thr Ile Ser Arg Asp Asn Ala Lys Asn Thr Leu Tyr
 65                  70                  75                  80
Leu Gln Met Ser Ser Leu Lys Ser Glu Asp Thr Ala Met Tyr Tyr Cys
                 85                  90                  95
Ala Arg Gly Asn Trp Glu Gly Trp Tyr Phe Asp Val Trp Gly Gln Gly
                100                 105                 110
Thr Thr Val Thr Val Ser Ser Gly Gly Gly Ser Gly Gly Gly Gly
                115                 120                 125
Ser Gly Gly Gly Ser Asn Ile Glu Leu Thr Gln Ser Pro Ala Ile
130                 135                 140
Met Ser Ala Ser Pro Gly Glu Arg Val Thr Met Thr Cys Ser Ala Ser
145                 150                 155                 160
Ser Ser Ile Arg Tyr Ile Tyr Trp Tyr Gln Gln Lys Pro Gly Ser Ser
                165                 170                 175
Pro Arg Leu Leu Ile Tyr Asp Thr Ser Asn Val Ala Pro Gly Val Pro
                180                 185                 190
Phe Arg Phe Ser Gly Ser Gly Ser Gly Thr Ser Tyr Ser Leu Thr Ile
                195                 200                 205
Asn Arg Met Glu Ala Glu Asp Ala Ala Thr Tyr Tyr Cys Gln Glu Trp
                210                 215                 220
Ser Gly Tyr Pro Tyr Thr Phe Gly Gly Gly Thr Lys Leu
225                 230                 235

<210> SEQ ID NO 10
<211> LENGTH: 9
<212> TYPE: PRT
<213> ORGANISM: Artificial sequence
<220> FEATURE:
<223> OTHER INFORMATION: Influenza derived HLA-restricted peptide

<400> SEQUENCE: 10

Gly Ile Leu Gly Phe Val Phe Thr Leu
1               5

<210> SEQ ID NO 11
<211> LENGTH: 9
<212> TYPE: PRT
<213> ORGANISM: Artificial sequence
<220> FEATURE:
<223> OTHER INFORMATION: Hepatitis B derived HLA-restricted peptide

<400> SEQUENCE: 11

Ser Thr Asn Arg Gln Ser Gly Arg Gln
1               5
```